(12) United States Patent
Knodel et al.

(10) Patent No.: US 8,636,189 B1
(45) Date of Patent: Jan. 28, 2014

(54) ACTIVE WEDGE FOR SURGICAL STAPLER

(75) Inventors: Bryan D. Knodel, Flagstaff, AZ (US);
Philipe R. Manoux, Oakland, CA (US);
Brendan M. Donohoe, Fairfax, CA (US)

(73) Assignee: Cardica, Inc., Redwood City, CA (US)

( * ) Notice: Subject to any disclaimer, the term of this patent is extended or adjusted under 35 U.S.C. 154(b) by 379 days.

(21) Appl. No.: 13/090,214

(22) Filed: Apr. 19, 2011

(51) Int. Cl.
*A61B 17/068* (2006.01)

(52) U.S. Cl.
USPC ....... 227/176.1; 227/19; 227/180.1; 606/139; 606/219

(58) Field of Classification Search
USPC ............... 227/19, 175.1, 175.2, 176.1, 178.1, 227/180.1; 606/139, 151, 153, 219
See application file for complete search history.

(56) References Cited

U.S. PATENT DOCUMENTS

| | | | |
|---|---|---|---|
| 1,939,631 A | 12/1933 | Randall | |
| 1,947,388 A | 2/1934 | Frey | |
| 2,127,665 A | 8/1938 | Leslie | |
| 2,568,969 A | 9/1951 | Reiss et al. | |
| 3,581,551 A | 6/1971 | Wilkinson | |
| 3,650,453 A | 3/1972 | Smith, Jr. | |
| 3,675,688 A | 7/1972 | Bryan et al. | |
| 3,717,294 A | 2/1973 | Green | |
| 3,837,555 A | 9/1974 | Green | |
| 3,899,914 A | 8/1975 | Akiyama | |
| 3,955,581 A | 5/1976 | Spasiano et al. | |
| 4,043,504 A | 8/1977 | Hueil et al. | |
| 4,086,926 A | 5/1978 | Green et al. | |
| 4,127,227 A | 11/1978 | Green | |
| 4,228,895 A | 10/1980 | Larkin | |
| 4,275,813 A | 6/1981 | Noiles | |
| 4,475,679 A | 10/1984 | Fleury, Jr. | |
| 4,523,707 A | 6/1985 | Blake, III et al. | |
| 4,556,058 A | 12/1985 | Green | |
| 4,589,416 A | 5/1986 | Green | |
| 4,633,861 A | 1/1987 | Chow et al. | |
| 4,655,222 A | 4/1987 | Florez et al. | |
| 4,719,917 A | 1/1988 | Barrows et al. | |
| 4,762,260 A | 8/1988 | Richards et al. | |
| 4,969,591 A | 11/1990 | Richards et al. | |
| 4,978,049 A | 12/1990 | Green | |
| 5,156,315 A | 10/1992 | Green et al. | |

(Continued)

FOREIGN PATENT DOCUMENTS

| EP | 1238634 | 9/1994 |
|---|---|---|
| EP | 1464287 | 10/2004 |

(Continued)

OTHER PUBLICATIONS

Gong, Shao W., "Perfectly flexible mechanism and integrated mechanism system design", *Mechanism and Machine Theory 39* (2004), (Nov. 2004),1155-1174.

(Continued)

*Primary Examiner* — Scott A. Smith
(74) *Attorney, Agent, or Firm* — Cardica, Inc.

(57) ABSTRACT

An exemplary active wedge for use with surgical staples, comprising a wedge base having an upper surface; and at least one wedge grate movable relative to the wedge base between a first position and a second position, where in the first position of the wedge base substantially all of the wedge grate is located below the upper surface of the wedge base, and where in the second position at least part of the wedge grate is positioned above the upper surface of the wedge base.

20 Claims, 24 Drawing Sheets

(56) References Cited

U.S. PATENT DOCUMENTS

| | | | |
|---|---|---|---|
| 5,170,925 A | 12/1992 | Madden et al. | |
| 5,192,288 A | 3/1993 | Thompson et al. | |
| 5,242,457 A | 9/1993 | Akopov et al. | |
| 5,269,792 A | 12/1993 | Kovac et al. | |
| 5,307,976 A | 5/1994 | Olson et al. | |
| 5,413,272 A | 5/1995 | Green et al. | |
| 5,415,334 A | 5/1995 | Williamson, IV et al. | |
| 5,452,836 A * | 9/1995 | Huitema et al. | 227/176.1 |
| 5,456,400 A | 10/1995 | Shichman et al. | |
| 5,476,206 A | 12/1995 | Green et al. | |
| 5,485,947 A * | 1/1996 | Olson et al. | 227/176.1 |
| 5,507,776 A | 4/1996 | Hempel | |
| 5,527,319 A | 6/1996 | Green et al. | |
| 5,547,117 A | 8/1996 | Hamblin et al. | |
| 5,547,474 A | 8/1996 | Kloeckl et al. | |
| 5,553,765 A | 9/1996 | Knodel et al. | |
| 5,620,289 A | 4/1997 | Curry | |
| 5,626,585 A | 5/1997 | Mittelstadt et al. | |
| 5,630,541 A | 5/1997 | Williamson, IV et al. | |
| 5,655,698 A | 8/1997 | Yoon | |
| 5,662,260 A | 9/1997 | Yoon | |
| 5,669,544 A * | 9/1997 | Schulze et al. | 227/176.1 |
| 5,692,668 A | 12/1997 | Schulze et al. | |
| 5,810,855 A | 9/1998 | Rayburn et al. | |
| 5,816,471 A | 10/1998 | Plyley et al. | |
| 5,826,776 A * | 10/1998 | Schulze et al. | 227/176.1 |
| 5,833,695 A | 11/1998 | Yoon | |
| 5,855,311 A | 1/1999 | Hamblin et al. | |
| 5,871,135 A | 2/1999 | Williamson, IV et al. | |
| 5,875,538 A | 3/1999 | Kish et al. | |
| 5,894,979 A | 4/1999 | Powell | |
| 5,918,791 A | 7/1999 | Sorrentino et al. | |
| 5,964,774 A | 10/1999 | McKean et al. | |
| 6,086,304 A | 7/2000 | Hujishima et al. | |
| 6,264,087 B1 | 7/2001 | Whitman | |
| 6,306,149 B1 | 10/2001 | Meade | |
| 6,391,038 B2 | 5/2002 | Vargas et al. | |
| 6,419,682 B1 | 7/2002 | Appleby et al. | |
| 6,443,973 B1 | 9/2002 | Whitman | |
| 6,478,804 B2 | 11/2002 | Vargas et al. | |
| 6,592,597 B2 | 7/2003 | Grant et al. | |
| 6,602,252 B2 | 8/2003 | Mollenauer | |
| 6,716,232 B1 | 4/2004 | Vidal et al. | |
| 6,817,508 B1 | 11/2004 | Racenet et al. | |
| 6,827,246 B2 * | 12/2004 | Sullivan et al. | 227/180.1 |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,111,768 B2 | 9/2006 | Cummins et al. | |
| 7,128,253 B2 | 10/2006 | Mastri et al. | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,258,262 B2 | 8/2007 | Mastri et al. | |
| 7,401,720 B1 | 7/2008 | Durrani | |
| 7,434,715 B2 | 10/2008 | Shelton, IV et al. | |
| 7,467,740 B2 | 12/2008 | Shelton, IV et al. | |
| 7,497,865 B2 | 3/2009 | Willis et al. | |
| 7,506,791 B2 | 3/2009 | Omaits et al. | |
| 7,517,356 B2 | 4/2009 | Heinrich | |
| 7,588,177 B2 | 9/2009 | Racenet | |
| 7,604,151 B2 | 10/2009 | Hess et al. | |
| 7,635,073 B2 | 12/2009 | Heinrich | |
| 7,635,373 B2 | 12/2009 | Ortiz | |
| 7,641,432 B2 | 1/2010 | Lat et al. | |
| 7,644,848 B2 | 1/2010 | Swayze et al. | |
| 7,731,072 B2 * | 6/2010 | Timm et al. | 227/175.1 |
| 7,934,631 B2 * | 5/2011 | Balbierz et al. | 227/176.1 |
| 8,365,971 B1 * | 2/2013 | Knodel | 227/175.1 |
| 8,439,246 B1 * | 5/2013 | Knodel | 227/180.1 |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2006/0241660 A1 | 10/2006 | Bombard et al. | |
| 2006/0253143 A1 | 11/2006 | Edoga et al. | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2008/0078807 A1 | 4/2008 | Hess et al. | |
| 2008/0272175 A1 | 11/2008 | Holsten et al. | |
| 2010/0179559 A1 | 7/2010 | Walker | |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

"Notification of Transmittal of the International Search Report and the Written Opinion of the International Searching Authority", PCT/US2008/075449, (Apr. 29, 2009).

"International Search Report", PCT/US2008/075449, (Apr. 29, 2009).

"Written Opinion of the International Searching Authority", PCT/US2008/075449, (Apr. 29, 2009).

"Cardica Microcutter Implant Delivery Device 510(k), Cover Sheet, Table 10.1, "Substantial Equivalence Comparison," and Section 12, "Substantial Equivalence Discussion"".

* cited by examiner

ACTIVE WEDGE FOR SURGICAL STAPLER

FIELD OF THE INVENTION

The invention generally relates to a surgical tool and method, and more specifically to an endocutter.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. The surgeon inserts the endocutter through a trocar or other port or incision in the body, orients the end of the endocutter around the tissue to be transected, and compresses the anvil and cartridge together to clamp the tissue. Then, a row or rows of staples are deployed on either side of the transection line, and a blade is advanced along the transection line to divide the tissue.

During actuation of an endocutter, the cartridge fires all of the staples that it holds. In known endocutters and linear staplers, wedges are moved longitudinally, where each wedge sequentially encounters a plurality of staple drivers during its travel. Those staple drivers convert the longitudinal motion of the wedges into vertical motion of the staples, driving the staples upward into an anvil. The wedges are simply solid pieces of metal or other material shaped in a way to facilitate contact between the wedges and the staple drivers.

BRIEF DESCRIPTION OF THE DRAWINGS

The use of the same reference symbols in different figures indicates similar or identical items.

DETAILED DESCRIPTION

Endocutter

Three Staple Rows

Figure 1:
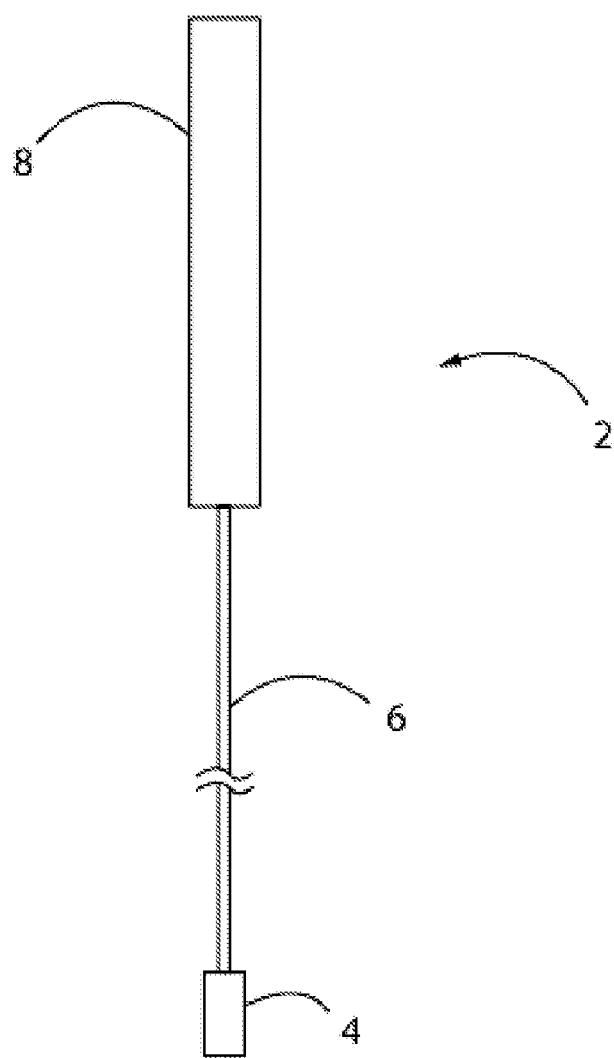
FIG. 1 is a schematic view of an endocutter.
Figure 2:
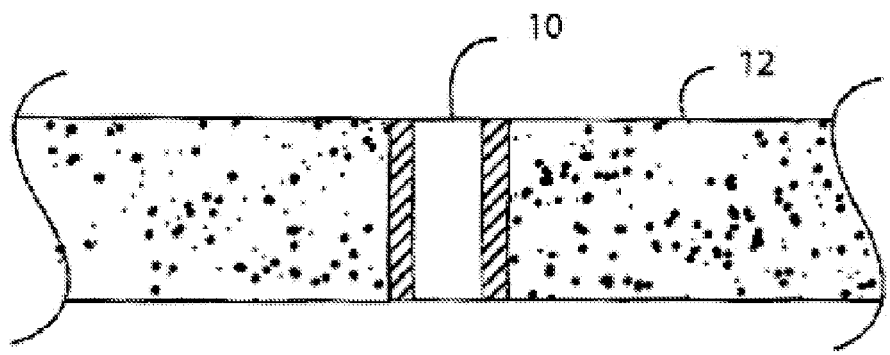
FIG. 2 is a cross-section view of a trocar port positioned in a patient.

Referring to FIG. 1, an endocutter 2 includes an end effector 4 attached to a shaft 6, which in turn is attached to a handle 8. The end effector 4 may be one or more separate components that are connected to the shaft 6, or may be fabricated integrally with the distal end of the shaft 6. Referring also to FIG. 2, the end effector 4 and the shaft 6 may be sized to pass through a standard trocar port 10 that may be placed through tissue 12 of a patient. Advantageously, the end effector 4 may be sized to pass through a trocar port 10 having an opening between 5-10 millimeters in diameter. Alternately, the endocutter 2 may be used in the course of conventional open surgery, where a trocar port is not used. Alternately, the endocutter 2 may be used in the course of minimally-invasive surgery, where access to the surgical site in the patient is gained through a mechanism or structure other than a trocar port, such as the LAP DISC® hand access device of Ethicon Endo-Surgery, Inc., or where access to the surgical site in the patient is gained through an incision or opening in which no port or other mechanism or structure is placed.

The trocar port 10 may be a hollow generally-tubular structure inserted into an incision in tissue 12 of a patient to hold that incision open and to prevent damage to the tissue 12 defining the incision opening that may result from the motion of tools and other objects through the incision. The trocar port 10 may be made from plastic or any other suitable biocompatible material. The trocar port 10 may have a substantially circular cross section, a substantially oval cross section, or any other suitable cross section. The particular dimensions of a trocar port 10 depend on the particular procedure to be performed on the patient, and may be any suitable dimensions. The trocar port 10 may be coupled to a cutting tool (not shown) through its center that makes an opening in tissue 12, after which the trocar port 10 is placed into tissue 12. The cutting tool may be a spike or other cutting or puncturing device, which is removed from the trocar port 10 when the trocar port 10 is in position in the chest wall. The combination of a trocar port 10 and a cutting tool is standard in the art.

Referring to FIG. 1, the shaft 6 of the endocutter 2 extends proximally from the end effector 4. The shaft 6 may be flexible or rigid. The shaft 6 may be articulated in at least one location, if desired. Optionally, the shaft 6 may include a cutaway, trough or other feature (not shown) to allow a guidewire (if any) or other positioning aid that may be used in the surgical procedure to remain in place during actuation of the endocutter 2.

The handle 8 may be attached to the proximal end of the shaft 6, or any other suitable portion of the shaft 6. The shaft 6 may be fabricated integrally with the handle 8. Alternately, the shaft 6 and the handle 8 may be two separate items that are connected together in any suitable manner. The handle 8 may include any mechanism, mechanisms, structure or structures that are suitably configured to actuate the end effector 4. The handle 8 may also include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in the U.S. patent application Ser. No. 11/054, 265, filed on Feb. 9, 2005, which is herein incorporated by reference in its entirety. The handle 8 may instead, or also, include a connector or connectors suitable for receiving stored energy from an external source, such as a hose connected to a hospital utility source of pressurized gas or of vacuum, or an electrical cord connectable to a power source.

Figure 3:
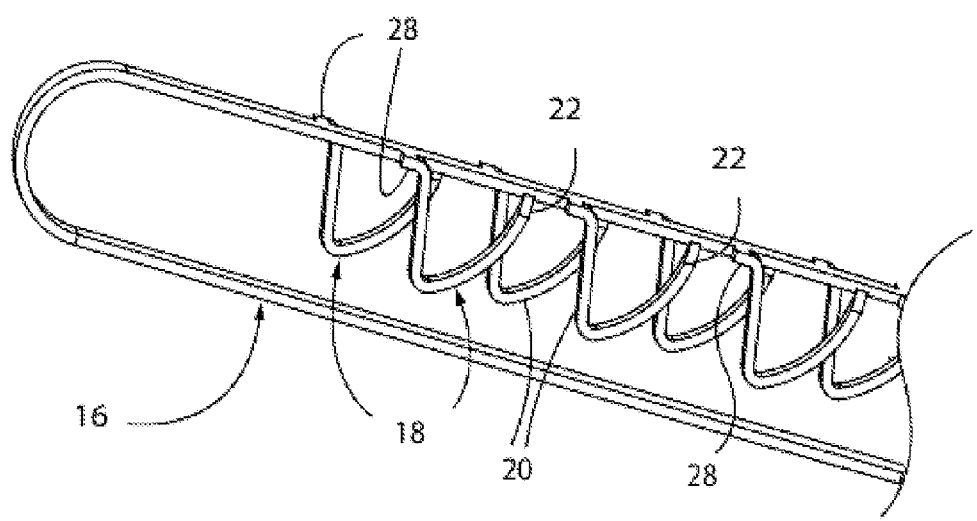
FIG. 3 is a perspective view of an exemplary feeder belt with three rows of staples frangibly connected thereto.
Figure 4:
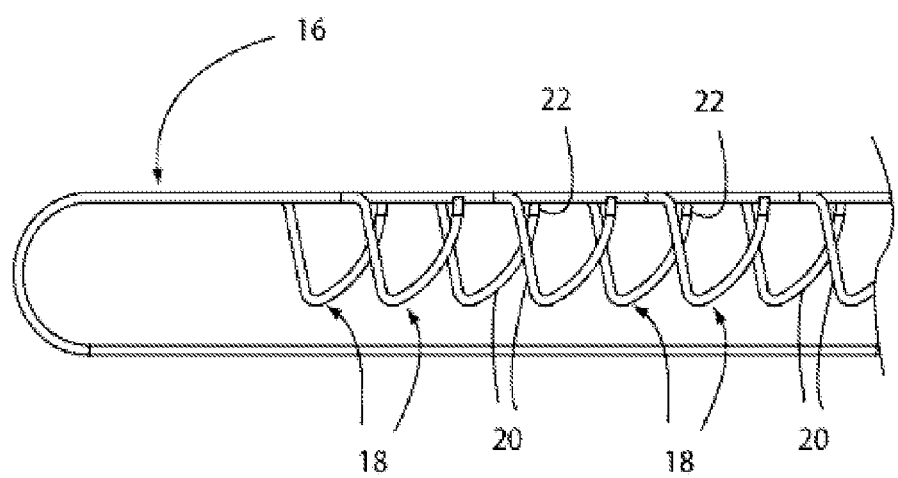
FIG. 4 is a side view of the feeder belt of FIG. 3.
Figure 5:
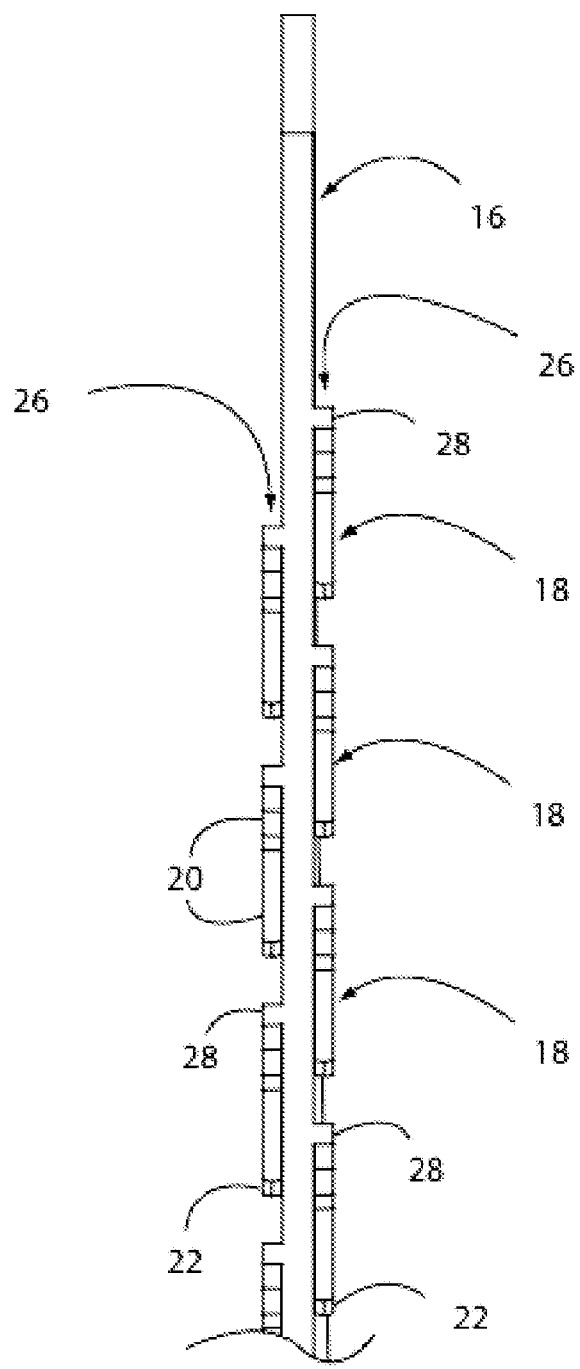
FIG. 5 is a top view of the feeder belt of FIG. 3.

Referring to FIGS. 3-5, a portion of a feeder belt 16 is positioned within the end effector 4. The feeder belt 16 may be a long, narrow, thin strip of material from which one or more staples 18 extend. The feeder belt 16 may be fabricated from stainless steel, nickel-titanium alloy, or any other suitable metallic or non-metallic material. The feeder belt 16 is flexible enough, and strong enough, to be advanced linearly and then redirected around a nose or other structure in substantially the opposite direction, as described in greater detail below. Alternately, the feeder belt 16 may be rigid or at least partially rigid, and may be advanced or retracted substantially linearly without redirection about a structure.

Two rows 26 of staples 18 may extend from the feeder belt 16. With such a feeder belt 16, one row 26 of staples 18 may be located along each side of the feeder belt 16. At least two staples 18 in different rows 26 may be staggered relative to one another. That is, at a given longitudinal position along the feeder belt 16 at which a staple 18 in one row 26 is attached to the feeder belt 16, the other row 26 does not have a staple 18 attached to the feeder belt 16. This staggering of the staples 18 promotes hemostasis in tissue treated with the end effector 4. Alternately, staples 18 in each row 26 may be aligned with one another, such that at a given longitudinal position along the feeder belt 16 at which a staple 18 in one row 26 is connected to the feeder belt 16, each other row 26 has a staple 18 connected to the feeder belt 16 as well.

The staples 18 in each row 26 may be substantially evenly spaced apart from one another. That is, the distance between any two longitudinally-adjacent staples 18 in a row is substantially the same. Alternately, at least two longitudinally-adjacent staples 18 in each row 26 may be spaced apart a distance different from the distance between two other longitudinally-adjacent staples 18. Such a configuration may be useful where the length of the staple line is not adjustable. The staple line to be created with the end effector 4 may be fixed at a particular number of staples 18, and the staples 18 in each row may be grouped together in groups each having a length substantially the same as that fixed staple line. Each group of staples 18 in a row 26 may thus be separated from the adjacent group of staples 18 by a blank space on the feeder belt 16, where that blank space may have any suitable length.

Each staple 18 may be shaped in any suitable manner; the staples 18 may be shaped substantially the same as one another, or may be shaped differently. As one example, each staple 18 is generally V-shaped, and has two legs 20 extending from the base of the V-shape. The base of the V-shape of the staple 18 may be curved, pointed or otherwise configured. One leg 20 of the staple 18 may be generally straight, and the other leg 20 of the staple 18 may be gently curved. However, the legs 20 may be shaped in a different manner. For example, both legs 20 may be curved. Further, each leg 20 may be shaped in the same manner. The staple 18 need not be symmetrical, but can be fabricated symmetrically if desired.

Figure 6:
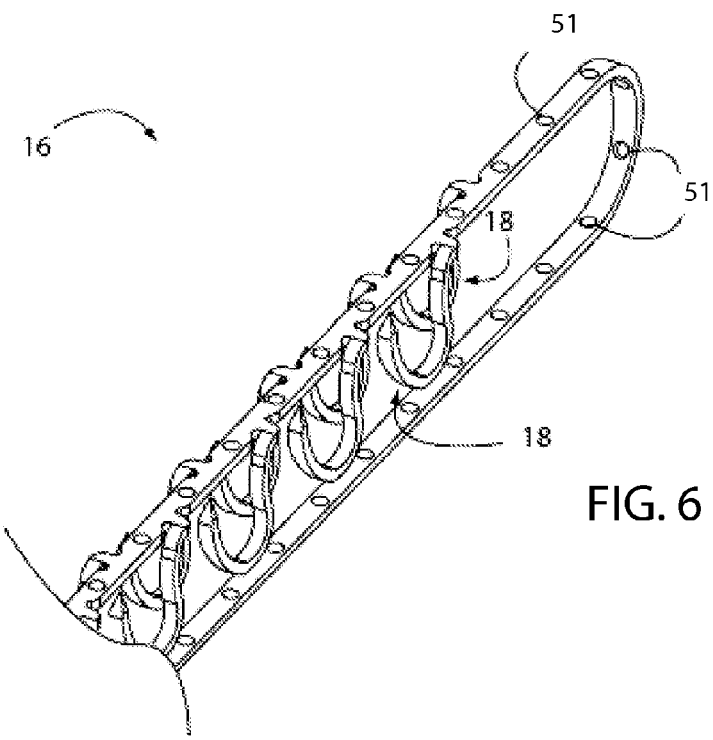
FIG. 6 is a perspective view of another exemplary feeder belt with two rows of staples frangibly connected thereto.
Figure 7:
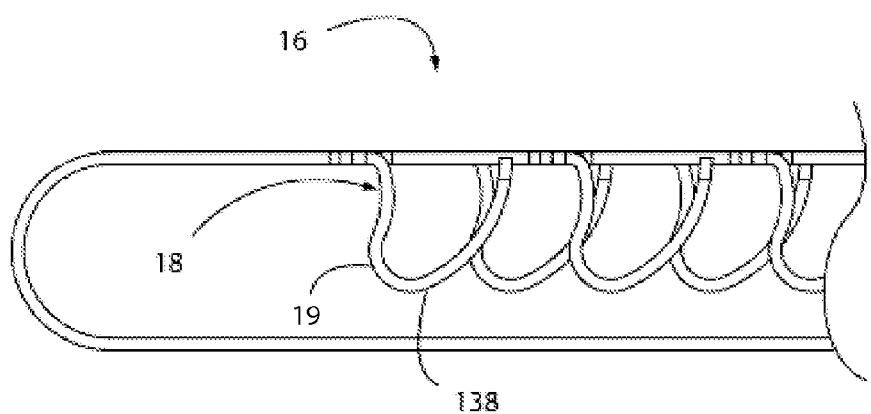
FIG. 7 is a side view of the feeder belt of FIG. 6.
Figure 8:
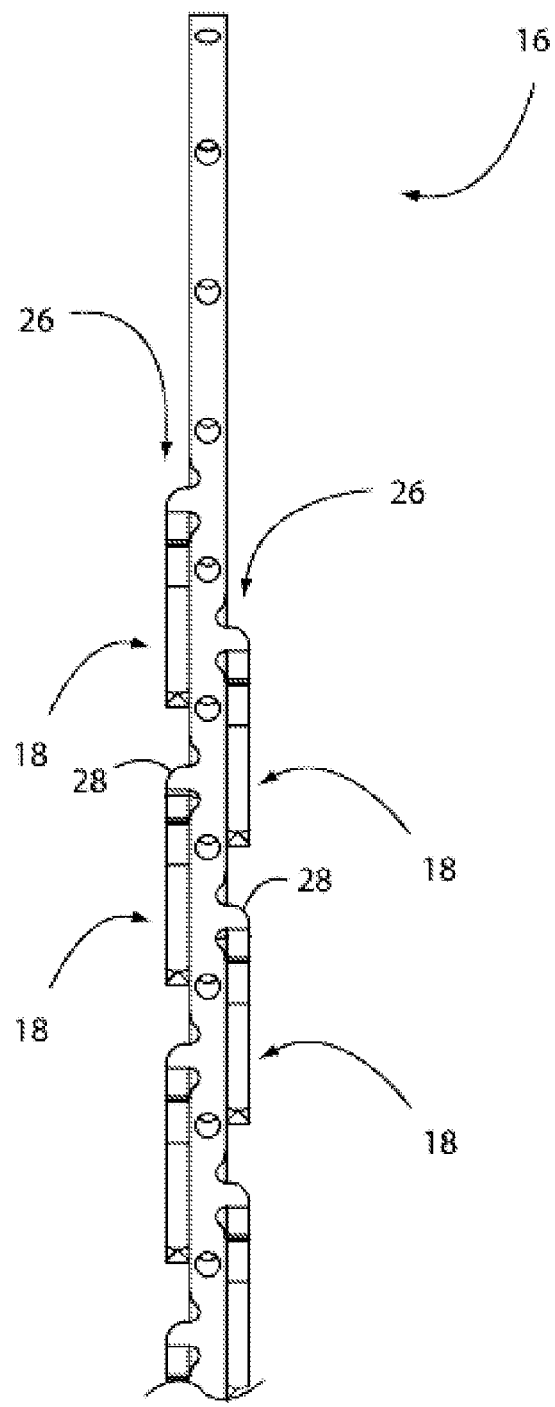
FIG. 8 is a top view of the feeder belt of FIG. 25.
Figure 26:
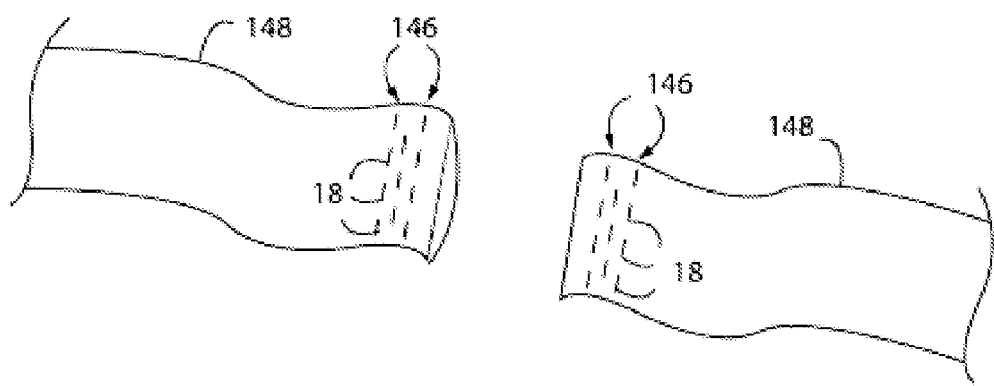
FIG. 26 is a perspective view of a blood vessel after transection by an endocutter.

As another example, referring also to FIGS. 6-8, at least one staple 18 may be shaped as a continuous curve, as may be most clearly seen in FIG. 26. A distal end of the staple 18 may be connected to the feeder belt 16, such as via a tab 28 protruding laterally from the feeder belt 16, such as described above. However, as used in this document, the term "tab" encompasses any frangible connection between the staple 18 and the feeder belt 16. Further, as used in this document, the terms "frangible" and "frangibly" have their ordinary meaning, which is "breakable." The staple 18 may extend proximally and downward from the tab 28. Then, the staple 18 may continue to curve downward, but also curve distally to form a bump 136. This bump 136 may extend to the longitudinal position of the tab 28, further distally than the longitudinal position of the tab 28, or not as far longitudinally as the tab 28. Then, the staple 18 may continue to curve downward, but also curve proximally. The staple 18 continues to curve proximally, then begins to curve upward at an inflection point 138. The staple 18 then continues to curve upward and proximally until terminating at a free end 22 at its proximal end.

One leg 20 of the staple 18 has a free end 22 that may be characterized as a tissue penetrating tip 22. The tissue penetrating tip 22 may be sharpened, if desired, to facilitate penetration of tissue. However, the legs 20 of the staple 18 may have a cross-section that is small enough that the tissue penetrating tip 22 need not be sharpened in order to easily penetrate tissue. The other leg 20 is attached at one end to the feeder belt 16. Advantageously, that leg 20 is frangibly connected to the feeder belt 16. Thus, one end of the staple 18 may be affixed to the feeder belt 16 and the other end of the staple 18 may be free. Alternately, the staple 18 may have three or more legs 20, or may be shaped in any other suitable manner.

The feeder belt 16 and staples 18 may be fabricated in any suitable manner. As one example, a flat, thin sheet of material is laser cut into long strips, after which each strip is laser cut to form fingers therein that are then bent into the shape of the staples 18. In this way, the staples 18 and the feeder belt 16 form an integral structure. However, the feeder belt 16 and staples 18 may be fabricated in any other suitable manner. As one example, the staples 18 and feeder belt are fabricated separately, and the staples 18 are then connected to the feeder belt 16 by welding, adhesive, or any other method that provides a frangible connection between the staples 18 and the feeder belt 16.

A frangible connection between the feeder belt 16 and each corresponding staple 18 may be configured in any suitable manner. As one example, referring particularly to FIG. 5, each feeder belt 16 may include at least one tab 28 protruding laterally therefrom, or defined laterally in the center thereof. Alternately, at least one tab 28 may be oriented differently. Advantageously, the tabs 28 result from laser cutting and subsequent mechanical deformation of the staples 18 during manufacturing, such that the tabs 28 and staples 18 are integral with the corresponding feeder belt 16. However, the tabs 28 and/or staples 18 may be fabricated and connected to the feeder belt 16 in any other suitable manner. At least one staple 18 may be attached to a corresponding tab 28 in any suitable manner. The attachment between a staple 18 and the corresponding tab 28 may be made in any suitable manner, and the connection between a staple 18 and the corresponding tab 28 may have any suitable orientation. As one example, at least one tab 28 is generally rectangular, and the corresponding staple 18 extends from the proximal edge of that rectangular tab 28. The staple 18 may be separable from the tab 28, at a location generally at the intersection between the staple 18 and the tab 28. The connection between a staple 18 and the corresponding tab 28 is strong enough to hold the staple 18 securely in place relative to the feeder belt 16 prior to deployment, and weak enough to be broken or otherwise separated from the tab 28 during or after deployment. Optionally, a staple 18 and/or tab 28 may include a weakened area at or near their intersection, in order to facilitate separation between the staple 18 and the feeder belt 16 during or after deployment. The weakened area may have a reduced cross-sectional area, may be notched, or otherwise structurally weakened. Alternately, the weakened area may also, or instead, be physically treated or otherwise configured to be weaker than the surrounding material, while having substantially the same physical dimensions as that surrounding material.

As shown in FIGS. 3-5, the staples 18 are in an initial configuration prior to being deployed. In the initial configuration, the staples 18 do not substantially contact one another. Alternately, at least two of the staples 18 may contact one another in the initial configuration. The staples 18 each may lie substantially in a single plane. That is, the staple 18 may be shaped such that a single plane extends through and substantially bisects the staple 18. Alternately, at least one staple 18 does not lie substantially in a single plane. At least one staple 18 may be positioned in a plane that is generally perpendicular to the feeder belt 16. Alternately, at least one staple 18 may be positioned in a plane that is angled differently relative to the feeder belt 16. One or more rows 26 of staples 18 are connected to the feeder belt 16. Each row 26 of staples 18 is the group of staples 18 positioned at substantially the same lateral location relative to the longitudinal centerline of the feeder belt 16, and each row 26 of staples 18 is oriented generally longitudinally. The feeder belt 16 may form a continuous loop, or may have a discrete beginning and end that are not attached to one another. Alternately, more or fewer rows 26 of staples 18 may be attached to the feeder belt 16. Each row 26 may extend along part, or all, or the length of the feeder belt 16. Different rows 26 may extend different lengths along the feeder belt 16.

Staples 18 in two or more different rows 26 along a single feeder belt 16 may be arranged in any suitable manner relative to one another. As one example, staples 18 in two or more different rows 26 along a single feeder belt 16 may be staggered relative to one another. That is, at a given longitudinal position along a single feeder belt 16 at which a staple 18 in one row 26 is attached to the feeder belt 16, at least one other row 26 does not have a staple 18 attached to that feeder belt 16. This staggering of the staples 18 promotes hemostasis in tissue treated with the end effector 4. Alternately, staples 18 in two or more of the rows 26 along a single feeder belt 16 may be aligned with one another, along at least part of the length of the rows 26, such that at a given longitudinal position along the feeder belt 16 at which a staple 18 in one row 26 is attached to the feeder belt 16, each other row 26 has a staple 18 attached to the feeder belt 16 as well. Alternately, staples 18 in two or more rows 26 along a single feeder belt 16 may be arranged differently along different longitudinal portions of that feeder belt 16. Staples 18 may be arranged relative to one another in the same manner, or differently, on different feeder belts 16 of the endocutter 2.

The staples 18 in each row 26 may be substantially evenly spaced apart from one another. That is, the distance between any two longitudinally-adjacent staples 18 in a row may be substantially the same. Alternately, at least two longitudinally-adjacent staples 18 in each row 26 may be spaced apart a distance different from the distance between two other longitudinally-adjacent staples 18. Such a configuration may be useful where the length of the staple line is not adjustable. The staple line to be created with the end effector 4 may be fixed at a particular number of staples 18, and consequently the staples 18 in each row may be grouped together in groups each having a length substantially the same as that fixed staple line. If so, each group of staples 18 in a row 26 may be separated from a adjacent group of staples 18 by a blank space on the feeder belt 16, where that blank space may have any suitable length. Advantageously, no staples 18 extend from, or into an area bounded by, the blank space of the feeder belt 16.

Figure 9:
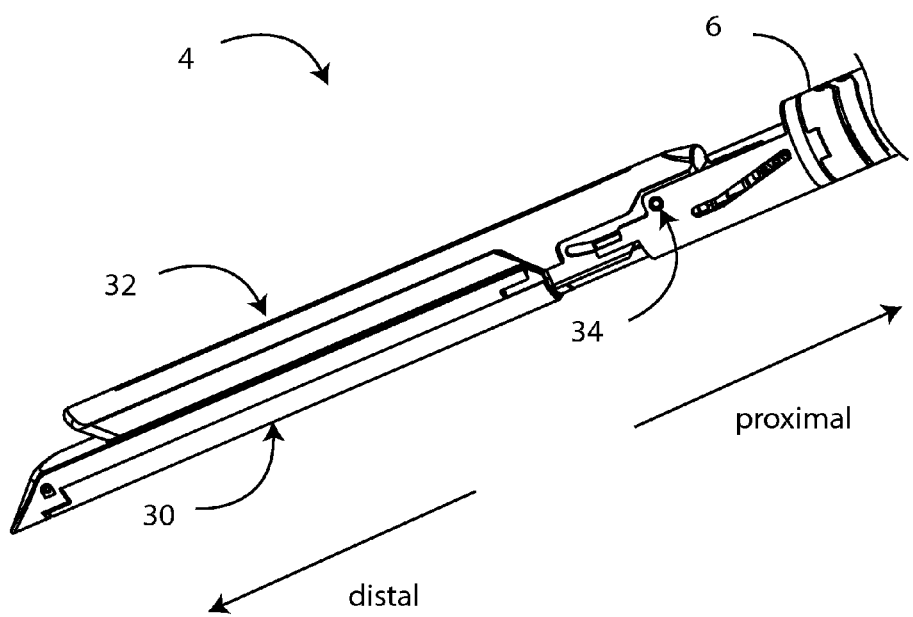
FIG. 9 is a perspective view of an exemplary end effector of an endocutter that utilizes a feeder belt.

Referring also to FIG. 9, the end effector 4 may include a staple holder 30 and an anvil 32. The anvil 32 may be movable about a pin 34 of other structure relative to the staple holder 30 to clamp and/or compress tissue therebetween in any suitable manner. The anvil 32 may include standard staple bending features defined therein to facilitate closure of the staples 18. Alternately, staple bending features may be omitted from the anvil 32. The anvil 32 may be pivotable relative to the staple holder 30. In this way, the distal end of the anvil 32 may be spaced apart from and positioned above the staple holder 30 in a first, initial position prior to clamping tissue, while the proximal end of the anvil 32 may be connected to the staple holder 30. Clamping of tissue by between the staple holder 30 and the anvil 32 may be performed in any suitable manner, and example of which is set forth in U.S. patent application Ser. No. 12/612,614, filed on Nov. 4, 2009, which is herein incorporated by reference in its entirety. Alternately, the anvil 32 may be connected to and/or movable relative to the staple holder in a different manner. Alternately, the staple holder 30 may be movable relative to the anvil 32. Alternately, the staple holder 30 and the anvil 32 may be movable relative to one another. The distal end of the staple holder 30 and the distal end of the anvil 32 may be blunt, in order to prevent inadvertent engagement of tissue with the end effector 4 during insertion of the end effector 4 into the patient and motion of the end effector 4 to a treatment site. Advantageously, the staple holder 30 is fixed to a remainder of the end effector 4 and/or the shaft 6, and is not detachable therefrom. As set forth in greater detail below, the staple holder 30 may be fired multiple times without being withdrawn from the patient, such that there is no need to withdraw the end effector 4 from the patient after each firing of staples 18 in order to replace a staple cartridge or other component. Nevertheless, if desired the staple holder 30 may be detachable from a remainder of the end effector 4 and/or the shaft 6; the end effector 4 may be detachable from the shaft 6; and/or the shaft 6 may be detachable from the handle 8.

Figure 10:
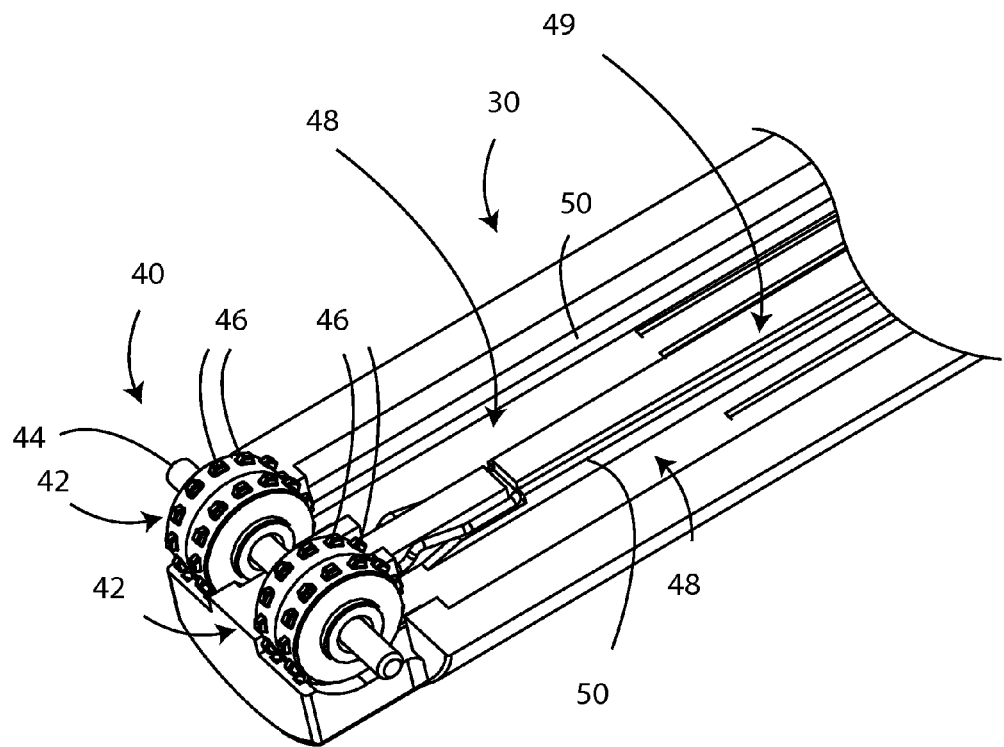
FIG. 10 is a perspective view of the interior of a staple holder of the endocutter of FIG. 1.

The staple holder 30 may include any suitable components. Referring also to FIG. 10, the staple holder 30 may include a feeder belt guide 40. The feeder belt guide 40 may be configured in any suitable manner. The feeder belt guide 40 may be located in proximity to the distal end of the staple holder 30. The feeder belt guide 40 may include one or more reversal wheels 42 that rotate about a reversal axle 44. Optionally, one or more reversal wheels 42 may include teeth 46 that engage corresponding apertures 51 in a feeder belt 16, as described in greater detail below. The reversal axle 44 may be held in place via fixation to a lateral part of the staple holder 30, which is omitted from FIG. 7 for clarity. The bottom inner surface 49 of the staple holder 30 may include one or more generally-longitudinal channels 48 defined therein. A step 50 may be defined on the lateral side of one or more channels 48, and may extend along some or all of the length of each channel 50. Each step 50 may be located slightly above and generally parallel to the lower surface of the corresponding channel 48. As another example of feeder belt guide 40, a feeder belt guide may be used as described in commonly-assigned U.S. Pat. App. Publication No. 2009/0065552 of Knodel et. al., published on Mar. 12, 2009, (the "Endocutter Document"), which is herein incorporated by reference in its entirety.

As used in this document, the term "upper" and similar terms of orientation mean a direction that is both perpendicular to the longitudinal centerline of the staple holder 30 and oriented toward the anvil 32. The term "lower" and similar terms of orientation refer to the direction opposite to the "upper" direction defined immediately above. The terms "distal" and "proximal" are used in the same manner as is standard to those of ordinary skill in the art, and refer to opposite directions along the longitudinal centerline of the staple holder 30, as illustrated in FIG. 10. The distal direction is oriented toward the free end of the staple holder 30, and the proximal direction is opposite to the distal direction.

Figure 11:
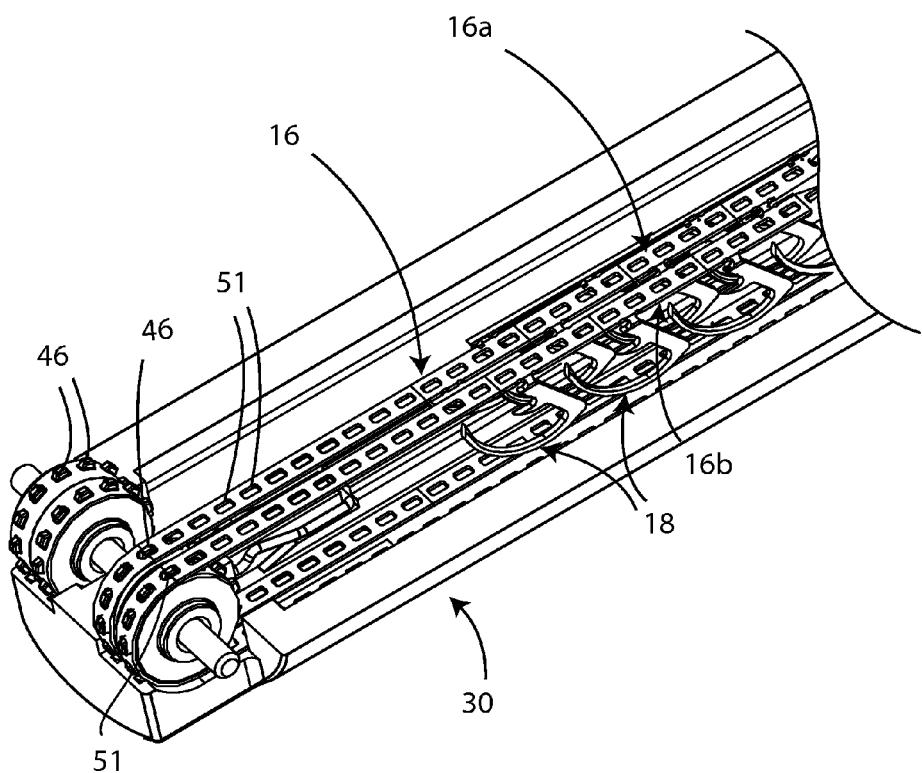
FIG. 11 is the perspective view of the interior of a staple holder of the endocutter of FIG. 7, with feeder belts shown.

Referring also to FIG. 11, the end effector 4 may include one or more feeder belts 16. In this way, staples 18 can be deployed on either side of an incision or transection to be made in tissue. Alternately, the end effector 4 may include only one feeder belt 16, or three or more feeder belts 16. The feeder belts 16 may be independent of one another, or connected to one another in any suitable manner. A feeder belt 16 may be routed around each reversal wheel 42. If provided, teeth 46 in one or more reversal wheels 42 may engage apertures 50 in a corresponding feeder belt or belts 16. Each feeder belt 16 may be routed along a path that starts generally straight and in the distal direction, then is curved along the surface of the corresponding reversal wheel 42, and then is generally straight and in the proximal direction. That is, the reversal wheel 42 changes the direction of motion of the corresponding feeder belt 16 from generally distal to generally proximal.

Figure 12:
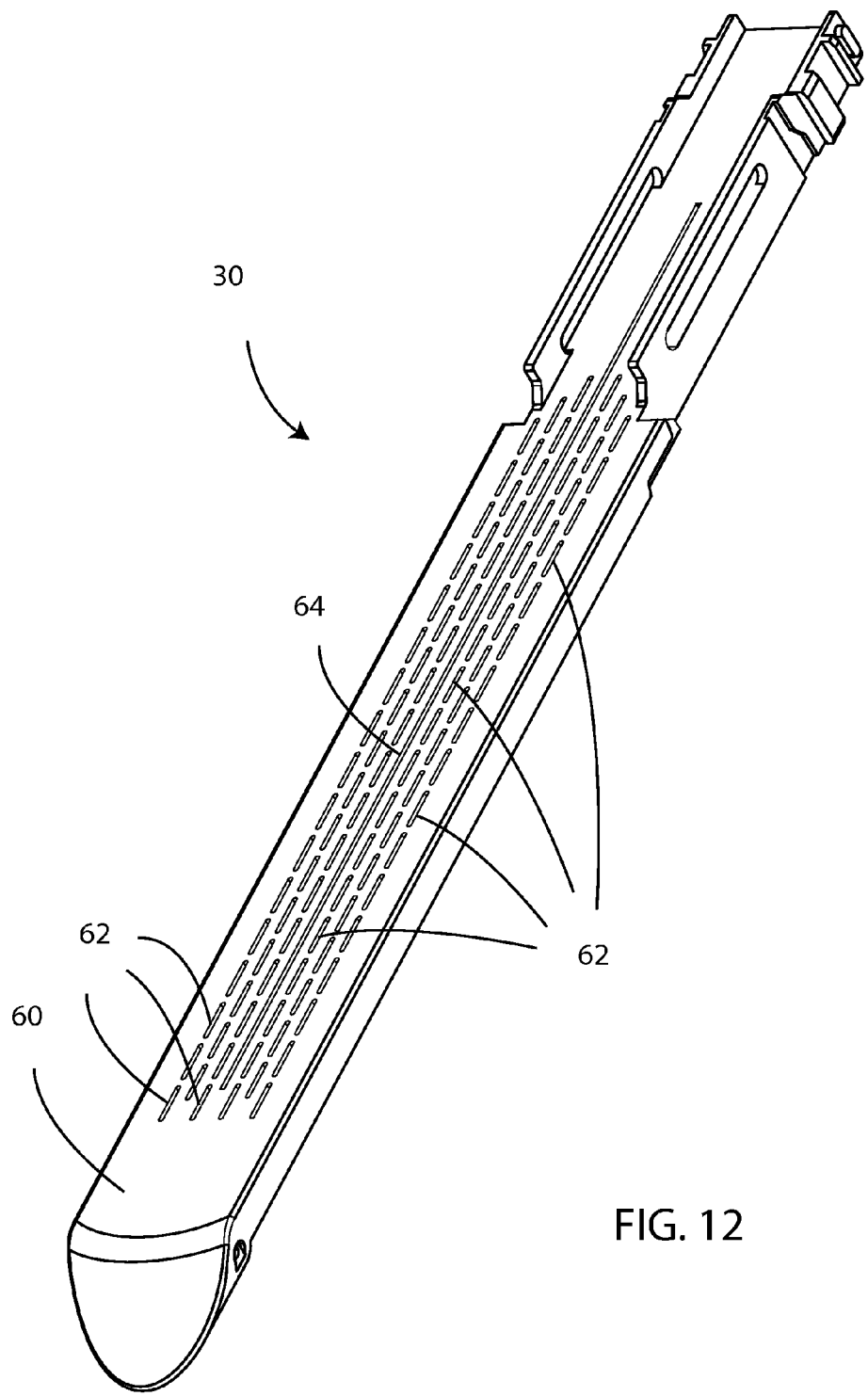
FIG. 12 is a perspective view of a staple holder.

The feeder belts 16 need not each contain the same number of staples 18. Referring to FIG. 12, a plurality of apertures 62 may be defined through the upper surface 60 of the staple holder 30, where the apertures 62 allow for deployment of staples 18 through the upper surface 60. The apertures 62 may be arranged into one or more longitudinally-oriented rows. As seen in FIG. 9, six longitudinally-oriented rows of apertures 62 may be provided. A knife slot 64 may be defined through the upper surface 60 of the staple holder 30 as well to allow for passage of a knife, as described in greater detail below. The rows of apertures 62 may be arranged symmetrically about the knife slot 64 as seen in FIG. 9, where three rows of apertures 62 are provided on each side of the knife slot 64. However, the apertures 62 may be arranged asymmetrically or otherwise arranged about the knife slot 64. Where three rows of apertures 62 are present on each side of the knife slot 64, two feeder belts 16 may be utilized, as seen in FIG. 11. If so, staples 18 may extend at an angle from each of two lateral edges of one feeder belt 16a, and staples 18 may extend at an angle from only one lateral edge of an adjacent feeder belt 16b. As another example, two identical feeder belts 16 may be provided, each of which includes staples 18 that extend at an angle from each of two lateral edges of the feeder belt 16, but staples 18 are only deployed from both lateral edges of one feeder belt 16; staples 18 are only deployed from one edge of the other feeder belt 16. An advantage of doing so is simplicity of manufacture, in that the manufacturer only need stock and track one type of feeder belt 16, rather than two separate feeder belts 16 each having a different number of staples 18.

Figure 13:
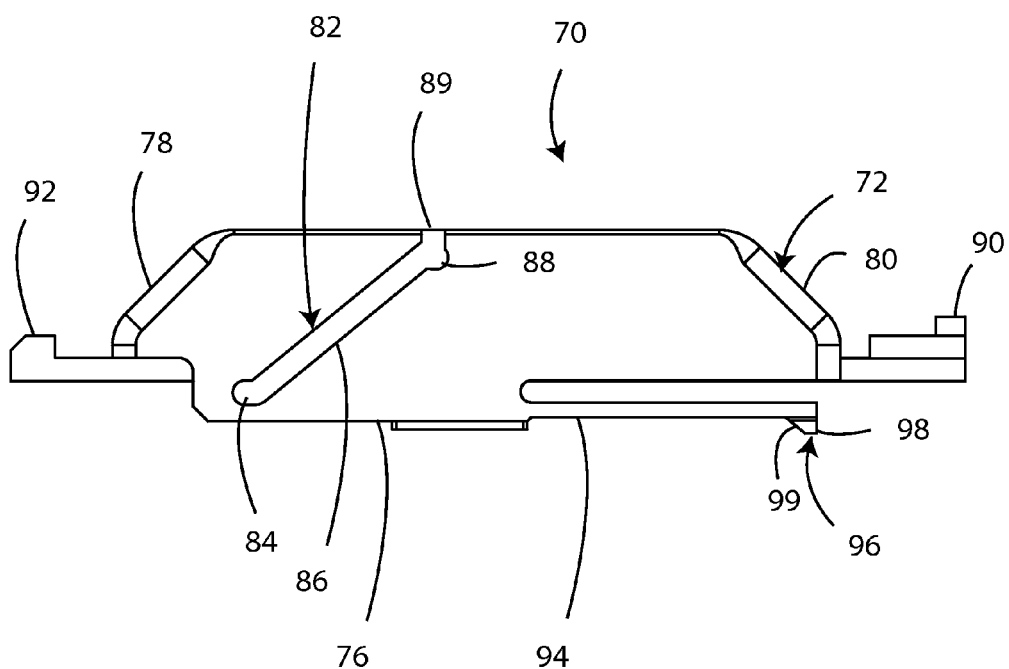
FIG. 13 is a side view of a wedge base.
Figure 14:
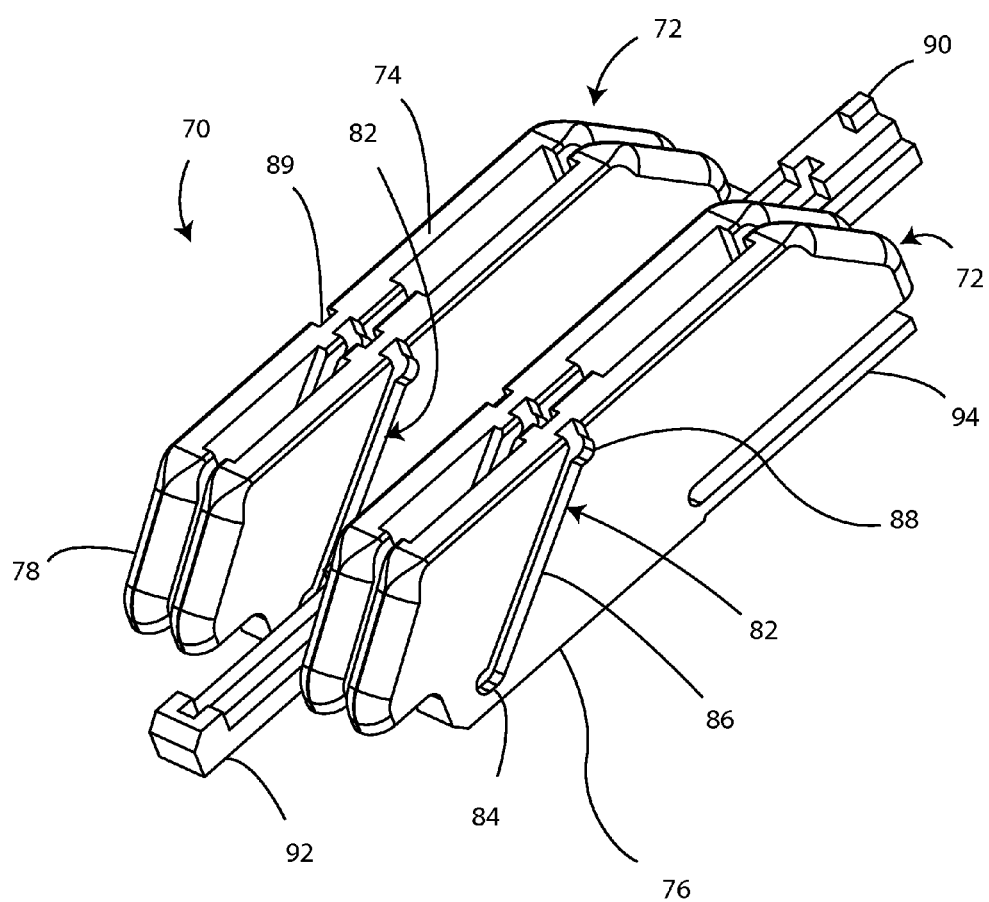
FIG. 14 is a perspective view of the wedge base of FIG. 13.
Figure 22:
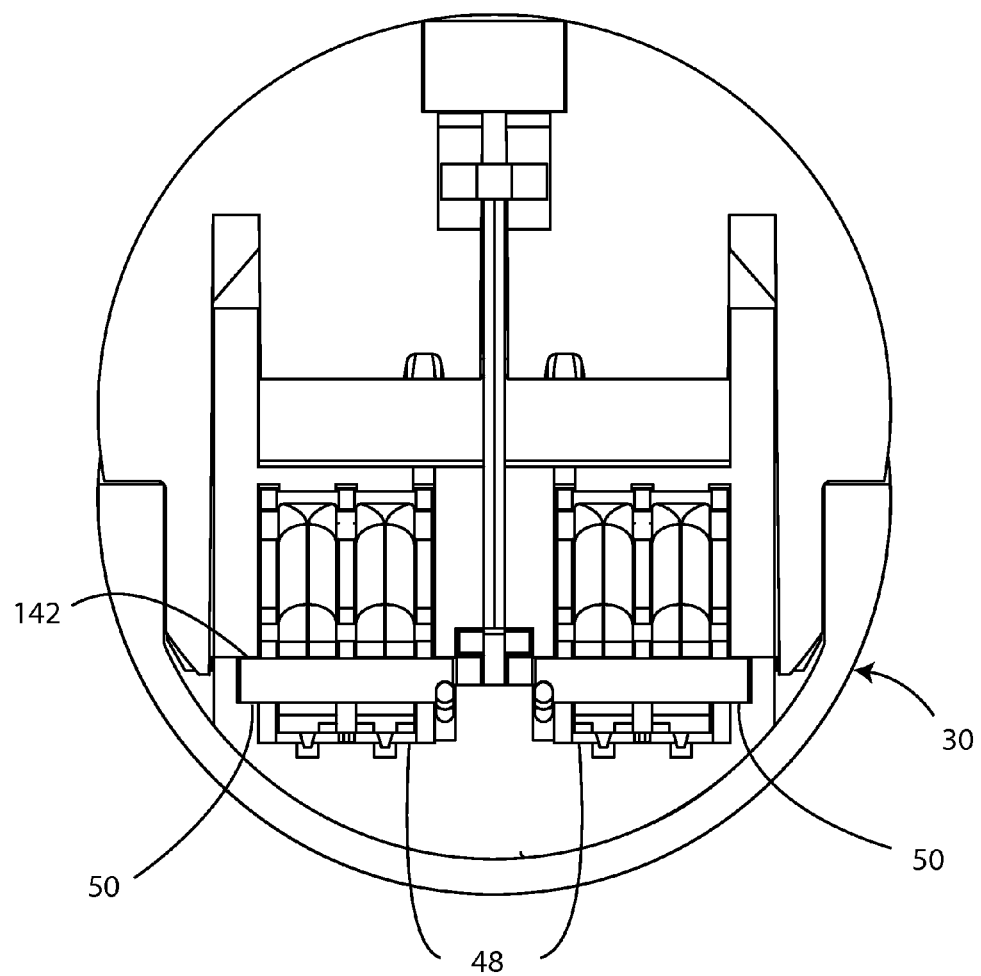
FIG. 22 is an end cross-section view of the active wedge of FIG. 15 in the second configuration of FIG. 21.

Referring to FIGS. 13-14, a wedge base 70 forms part of an active wedge, as described in greater detail below. The wedge base 70 includes one or more bulkheads 72. Referring also to FIG. 22, each bulkhead 72 is sized to fit underneath a corresponding feeder belt 16. Each bulkhead 72 has a width generally similar to the width of the corresponding feeder belt 16. In this way, each bulkhead 72 has a width that allows the bulkhead 72 to slide longitudinally along a corresponding feeder belt 16 between the staples 18 affixed to the feeder belt 16. Referring back to FIGS. 13-14, as one example, the bulkheads 72 may be arranged into two groups of two, where each group is laterally spaced from the other a distance greater than the distance between the bulkheads 72 in a single group. Each bulkhead 72 may have an upper surface 74. The upper surface 74 may contact, or be spaced apart vertically from, the corresponding feeder belt 16. Each bulkhead 72 may have a lower surface 76. The lower surface 76 may be generally parallel to the upper surface 74. Alternately, the lower surface 76 may be shaped and/or oriented in a different manner. Each bulkhead 72 may have a front surface 78, which may take any suitable shape. As one example, the front surface 78 may be angled upward in the proximal direction. Similarly, each bulkhead 72 may have a rear surface 80, which may take any suitable shape. As one example, the rear surface 80 may be angled downward in the proximal direction.

A channel 82 may be defined in each lateral side of each bulkhead 72. The channels 82 allow for motion of a wedge grate relative to the wedge base 70, as described in greater detail below. The channel 82 may have any suitable shape. As one example, the distal end 84 of the channel 82 is also the lowest end of the channel 82. The channel 82 may include a central segment 86 that is angled upward in the proximal direction from the distal end 84. The distal end 84 may extend a short distance distal to the distal end of the central segment 86, and that distal end 84 may extend generally longitudinally. In this way, the central segment 86 is angled relative to the distal end 84. At the upper, proximal end of the central segment 86, a detent 88 may be positioned. That is, the channel 82 defines a detent at its most proximal location. The detent 88 may extend a short distance proximal to the proximal end of the central segment 86, generally longitudinally. Above the detent 88, the upper end of the channel 82 may include an insertion aperture 89.

The wedge base 70 may include a boss 90. The boss 90 may be located at or near the proximal end of the wedge base 70, generally along the longitudinal centerline thereof. Alternately, the boss 90 may be located at any suitable position on the wedge base 70. The boss 90 may be positioned proximal to the bulkheads 72, or may be positioned differently relative to the bulkheads 72. Optionally, the wedge base 70 may include a knife mount 92. The knife mount 92 to be located at or near the distal end of the wedge base 70, generally along the longitudinal centerline thereof. Alternately the knife mount 92 may be located at any suitable position on the wedge base 70. The knife mount 92 be positioned distal to the bulkheads 72, or may be positioned differently relative to the bulkheads 72. The wedge base 70 may include one or more return arms 94. Each return arm 94 may be oriented generally longitudinally, and may be cantilevered proximally from a part of the lower surface 76 of the wedge base 70. In this way, the proximal end of the return arm is movable vertically at its proximal end. At the proximal end of the return arm 94, a tooth 96 extends downward. The proximal face of the tooth 96 may be a substantially vertical plane 98, and the distal face of the tooth 96 may be a substantially planar surface 99 angled downward in the proximal direction.

Figure 15:
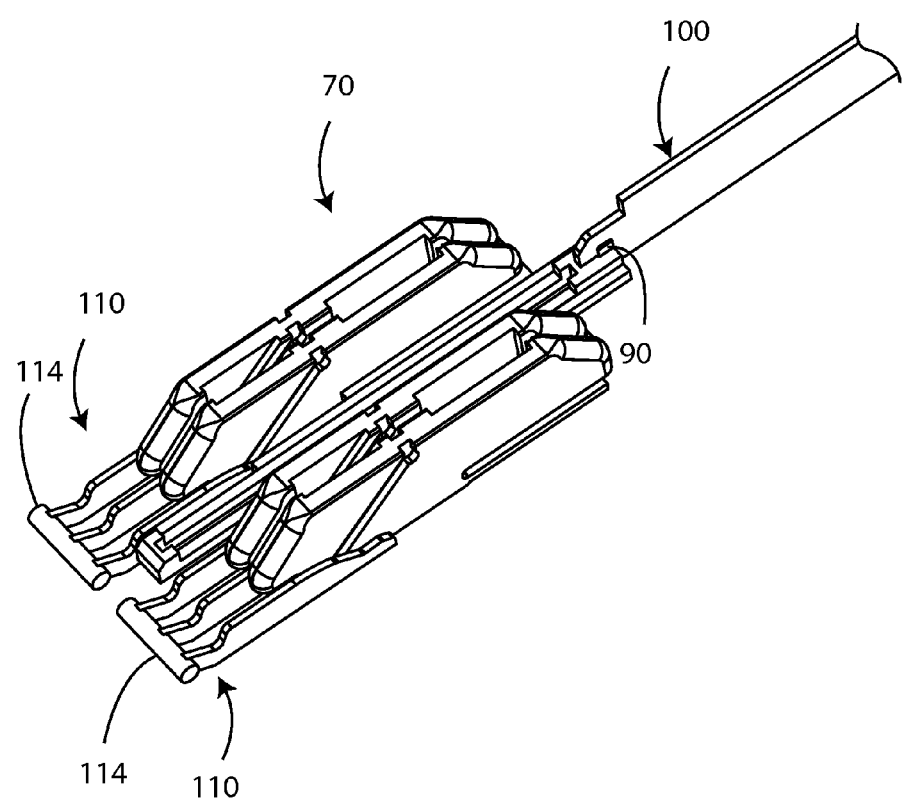
FIG. 15 is a perspective view of an active wedge.

Referring also to FIG. 15, an actuation band 100 is connected to the boss 90. Advantageously, the actuation band 100 is fixed to the boss 90 in any suitable manner. Alternately the actuation band 100 may be removable from the boss 90. The actuation band 100 may have any suitable shape, and may be fabricated from any suitable material, such as but not limited to stainless steel. As one example, the actuation band 100 may be generally rectangular in cross-section, where the lateral width of the actuation band 100 spans a lesser distance than the vertical height of the actuation band 100. In this way, the actuation band 100 may have some lateral flexibility to allow it to pass through an articulation in the shaft 6, while still providing vertical stiffness. The actuation band 100 is axially stiff enough for it to both push the wedge base 70 distally and pull the wedge base 70 proximally. The actuation band 100 may extend from the wedge base 70 through the entirety of the shaft 6 into the handle 8.

Figure 16:
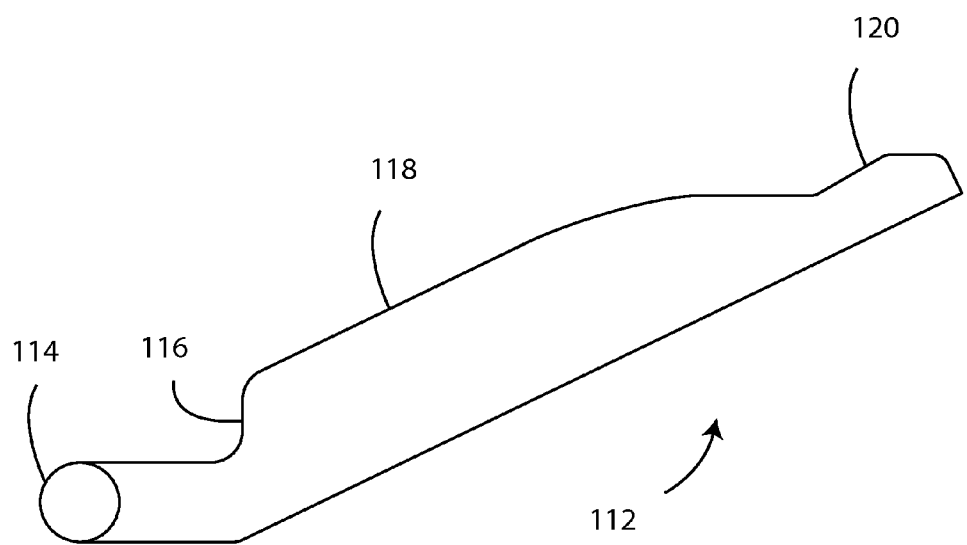
FIG. 16 is a side view of a first exemplary wedge plate.
Figure 17:
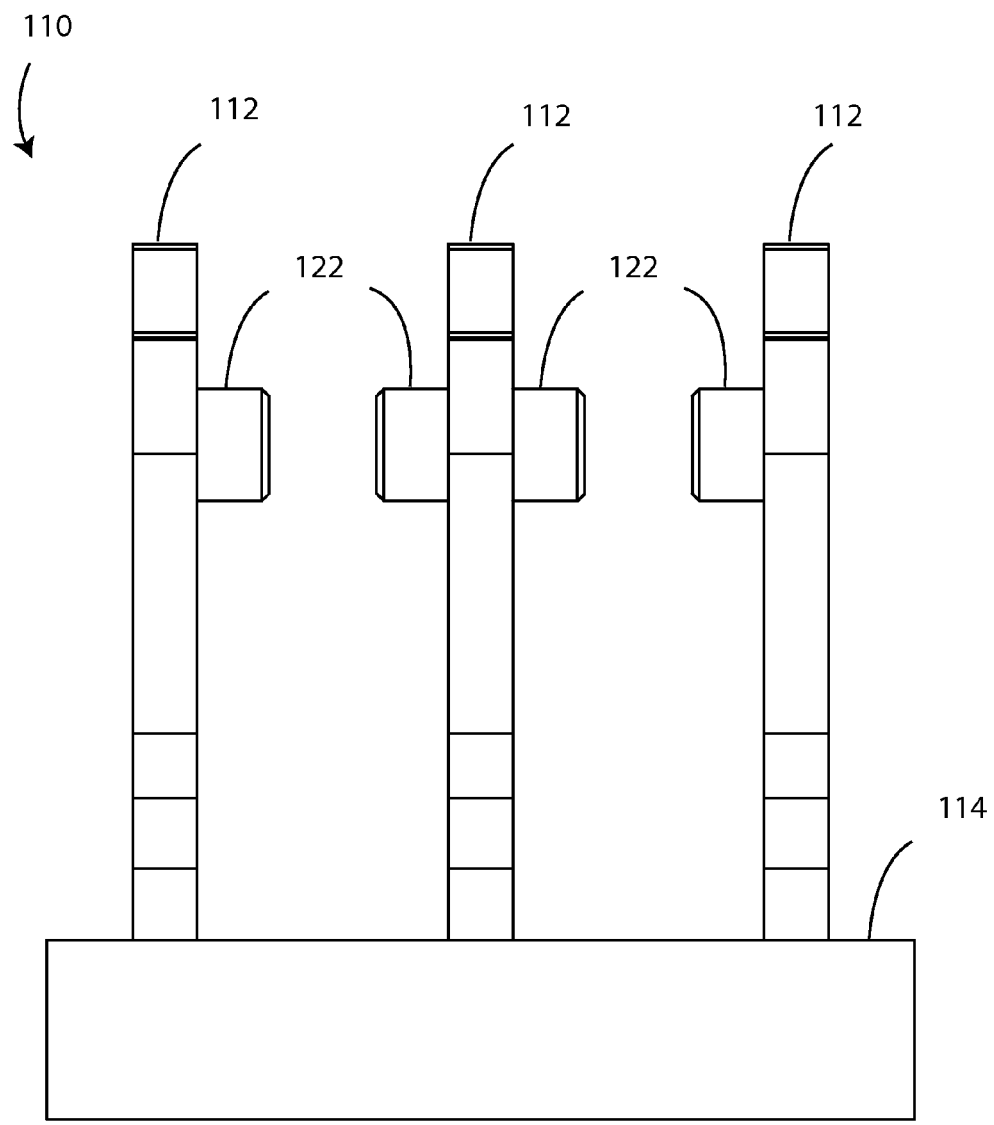
FIG. 17 is an end view of a wedge grate.

Referring also to FIGS. 16-17, at least one wedge grate 110 is movably connected to the wedge base 70. Each wedge grate 110 includes at least one wedge plate 112. The wedge plates 112 may be substantially planar, and substantially parallel to one another within the same wedge grate 110. A cross pin 114 may connect the distal ends of the different wedge plates 112 of the wedge grate 110. The cross pin 114 may be generally cylindrical. The cross pin 114 may have any other suitable shape; for example, a rectangular or triangular solid. As described in greater detail below, at least one wedge plate 112 sequentially contacts staples 18 along a longitudinal row along a feeder belt 16, first deforming a staple 18 and then breaking that staple 18 from the feeder belt 16. Each wedge plate 112 may have any suitable shape. As one example, referring to FIG. 16, a wedge plate 112 may include an encounter surface 116, a deformation surface 118, and a separation surface 120. The encounter surface 116 may be substantially vertical. Proximal to the encounter surface 116, the deformation surface 118 may extend upward in the proximal direction, where the deformation surface 118 is substantially a straight line. The surfaces 116, 118 may be immediately adjacent to one another, or maybe longitudinally separated any suitable distance. Proximal to the deformation surface 118, the separation surface 120 may extend further upward in the proximal direction. The surfaces 118, 120 may be immediately adjacent to one another, or maybe longitudinally separated any suitable distance. As another example, referring to FIG. 18, the encounter surface 116 may extend vertically a shorter length than the encounter surface 116 of FIG. 16. The deformation surface 118 may be smoothly curved, and may be a convex surface. As another example, each wedge plate 112 may have any other suitable shape. The wedge plates 112 in a single wedge grate 110 may all have substantially the same shape. Alternately, at least one wedge plate 112 within a wedge grate 110 they be shaped differently than at least one other wedge plate 112.

Each wedge plate 112 has at least one pin 122 extending therefrom. Each pin 122 is received in a corresponding channel 82 in the wedge base 70. During assembly, the pins 122 may be inserted into the corresponding insertion apertures 89 of the channels 82. Advantageously, each bulkhead 72 of the wedge base 70 includes channels 82 on both lateral sides thereof. Wedge plates 112 may be positioned lateral to each lateral side of each bulkhead 72. The term "active wedge" is defined to mean the combination of the wedge base 70 with at least one wedge grate 110 movably connected thereto. Referring to FIG. 15, where two groups of two bulkheads 72 are utilized, two wedge grates 110 may be utilized, where each wedge grate 110 is associated with a corresponding group of two bulkheads 72. One wedge plate 112 may be positioned laterally inward from the innermost lateral side of the innermost bulkhead 72; another wedge plate 112 may be positioned between the bulkheads 72 in the same group, and the third wedge plate 112 may be positioned laterally outward from the outermost lateral side of the outermost bulkhead 72.

Figure 18:
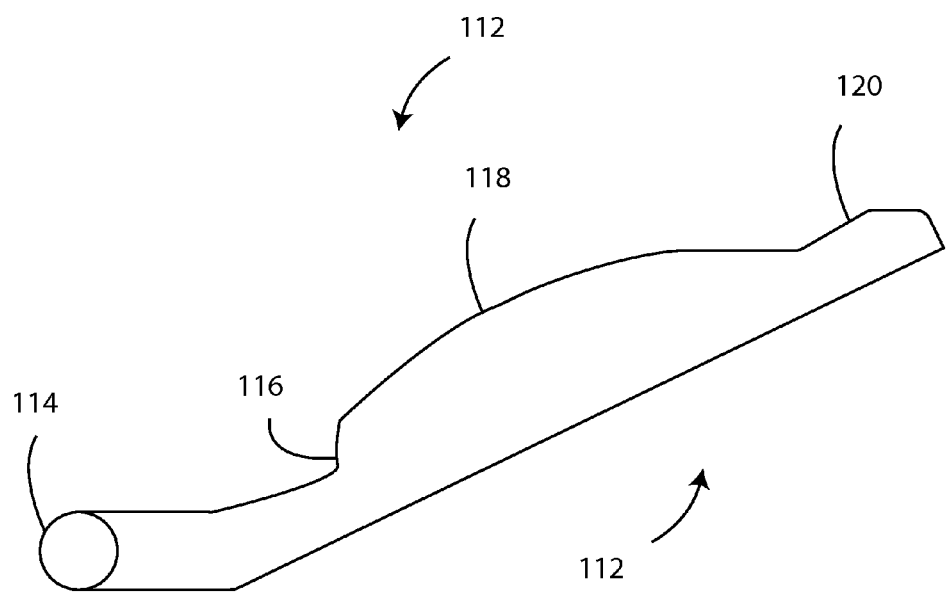
FIG. 18 is a side view of a second exemplary wedge plate.
Figure 19:
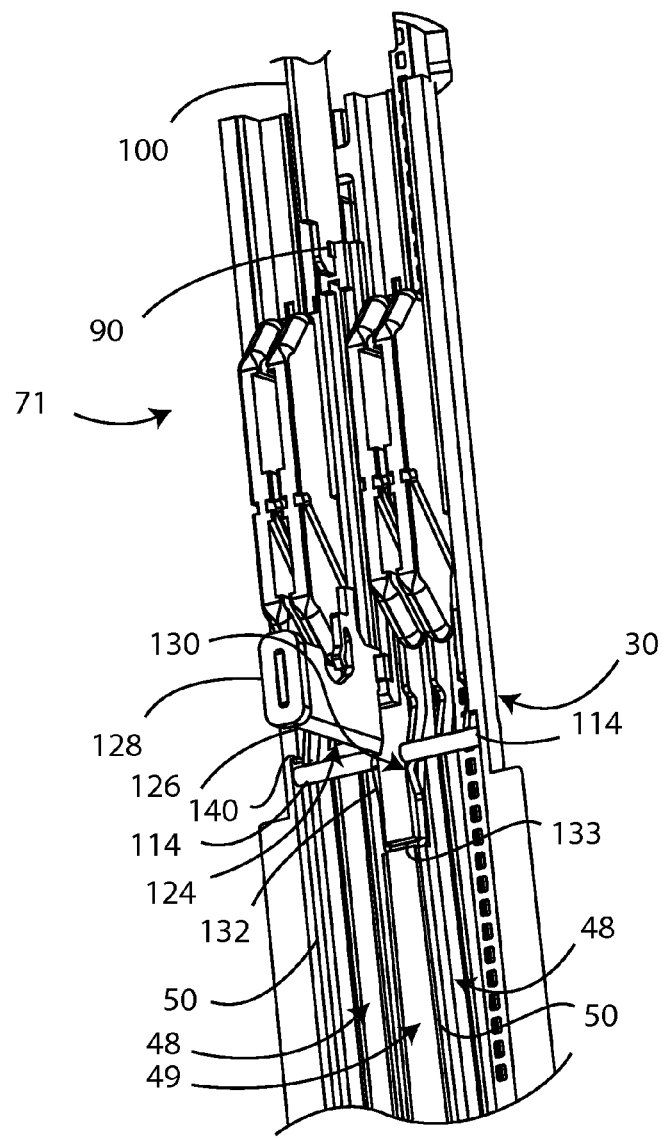
FIG. 19 is a perspective view of the active wedge of FIG. 15 at a first position within the staple holder, in a first configuration, showing a knife.

Referring to FIG. 18, a knife 124 may be connected to the knife mount 92 of the wedge base 70, or to any other suitable portion of the wedge base 70. The knife 124 may have a sharp edge 126 that is substantially vertical and that is at the distal edge of the knife 124. Alternately, the sharp edge 126 may be shaped and/or oriented differently. Optionally, an I-beam head 128 may be positioned at the top of the knife 124, or at any other suitable location on the knife 124. The I-beam head 128 may be received in a corresponding cavity within the anvil 32, and may slide along that cavity to facilitate clamping.

Figure 24:
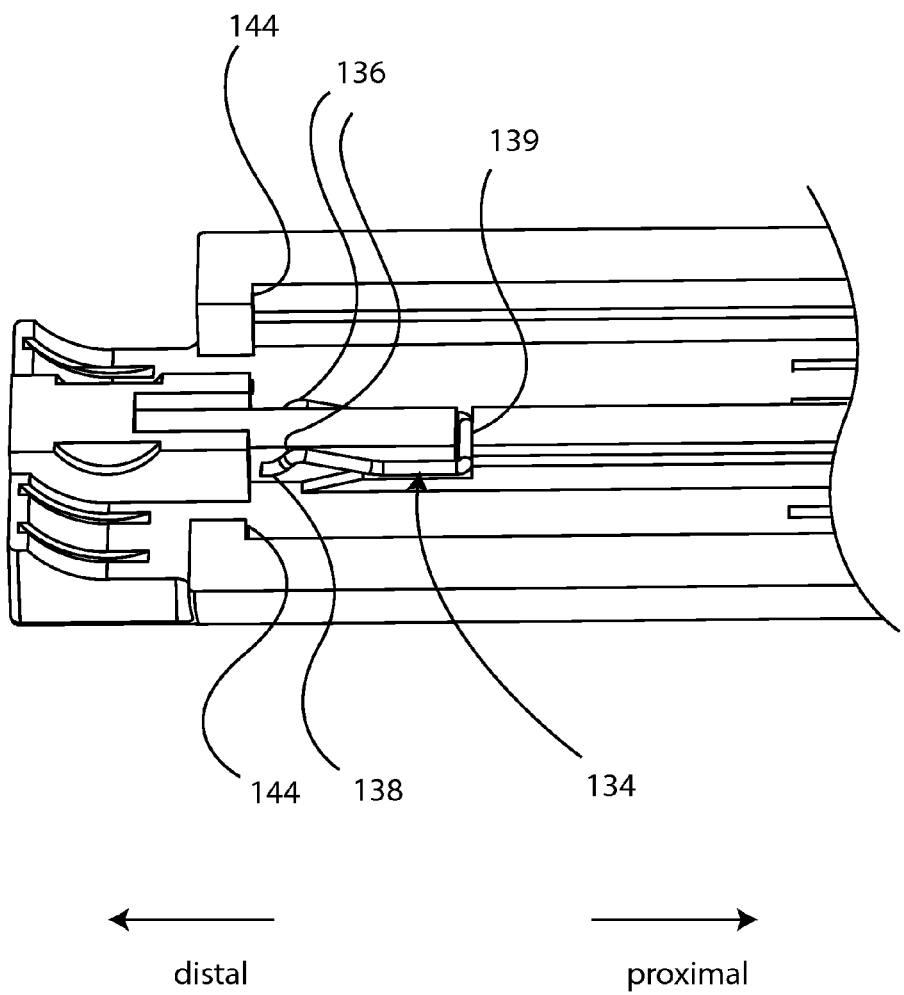
FIG. 24 is a perspective view of a wedge catch within the staple holder.

A proximal wedge catch 130 may be fastened to the bottom inner surface 49 of the staple holder 30. The proximal wedge catch 130 may be a wire or wire spring that slopes upward in the proximal direction to a peak 132, then slopes downward to a proximal end that is lower than the peak 132. The proximal wedge catch 130 may be generally U-shaped, or may define a closed perimeter. The distal end of the proximal wedge catch 130 may be held in a notch 133 in the bottom inner surface 49 of the staple holder 30. Referring also to FIG. 24, distal to the proximal wedge catch 130, in proximity to the distal end of the staple holder 30, a distal wedge catch 134 may be fastened to the bottom inner surface 49 of the staple holder 30. The distal wedge catch may be a wire or wire spring that slopes upward in the distal direction to a peak 136, then slopes downward to a distal end 138 that is lower than the peak 136. The distal wedge catch 134 may be generally U-shaped, or may define a closed perimeter. The proximal end of the distal wedge catch 134 may be held in a notch 139 in the bottom inner surface 49 of the staple holder 30.

Operation

Referring to FIG. 2, at least one trocar port 10 may be inserted into an opening in tissue 12 of a patient 14. Where a trocar port 10 includes a cutting tool (not shown) such as a spike, that cutting tool makes an opening in tissue 12, after which the trocar port 12 is placed in tissue. The cutting tool may be removed from the trocar port 10 after the trocar port 10 is in position in tissue 12. Alternately, an opening in tissue 12 may be made first with a separate tool, and the trocar port 10 is then placed in that opening. Multiple trocar ports 10, having the same or different cross-sectional shapes and/or areas, may be placed in the patient 14. The tissue 12 may be the chest wall of the patient 14, thereby providing access to the thoracic cavity. However, the tissue 12 may be the abdominal wall or any other suitable tissue in the patient 14. Alternately, the trocar port or ports 10 are not used, and access to the surgical site is gained in another manner, such as described above.

Referring also to FIGS. 1 and 9, the user of the endocutter 2, a medical professional such as a surgeon, then receives the endocutter 2. "Receiving" the endocutter 2 means that the user takes the endocutter 2 in hand, either directly from out of its package, or indirectly via a nurse, medical technician or other person. The end effector 4 of the endocutter 2 may be introduced into the patient 14 through one of the trocar ports 10. Referring to FIG. 9, the end effector 4 may be inserted into the patient 14 in a closed configuration. At least part of the shaft 6 of the endocutter 2 may follow the end effector 4 into the patient 14. Alternately, the trocar port or ports 10 are not used, and the endocutter 2 is used during a conventional open surgical procedure or is introduced into the patient 14 directly through an incision in tissue 12. The end effector 4 is positioned by the user at a surgical site. As one example, referring also to FIG. 26, a surgical site is located on a blood vessel 148 which is to be transected. For clarity, this document describes the operation of the endocutter 2 for transection of a blood vessel 148. However, the use of the endocutter 2 is not limited to blood vessel transection; the endocutter 2 may be used to perform any other suitable procedure at any other surgical site in the body. For example, the endocutter 2 may be used to transect a bile duct, to remove a diseased appendix, to transect gastrointestinal tissue, to remove a diseased lobe of a lung or liver, and/or to transect soft tissue or organs.

As set forth in the Endocutter Document, at least the distal end of the anvil 32 is initially spaced apart from the staple holder 30, such that the end effector 4 is open. The end effector 4 is advanced over the blood vessel 148 to be transected, until the entire diameter of the blood vessel 148 is located between the anvil 32 and the staple holder 30. Advantageously, the blood vessel 148 is substantially at a right angle to the anvil 32 and the staple holder 30. However, the blood vessel 148 may be oriented at any other suitable angle relative to the anvil 32 and the staple holder 30. The end effector 4 is then closed, by moving the anvil 32 closer to the staple holder 30, such that the blood vessel 148 is compressed between the anvil 32 and the staple holder 30. Such closure of the end effector 4 may be accomplished as set forth in the Endocutter Document. Closure of the end effector 4 may be performed by actuating one or more controls on the handle 8 of the endocutter 2, and/or by releasing energy stored in the handle 8. After the end effector 4 has been closed, the tissue to be treated is held securely by, and affirmatively controlled by, the end effector 4.

Figure 20:
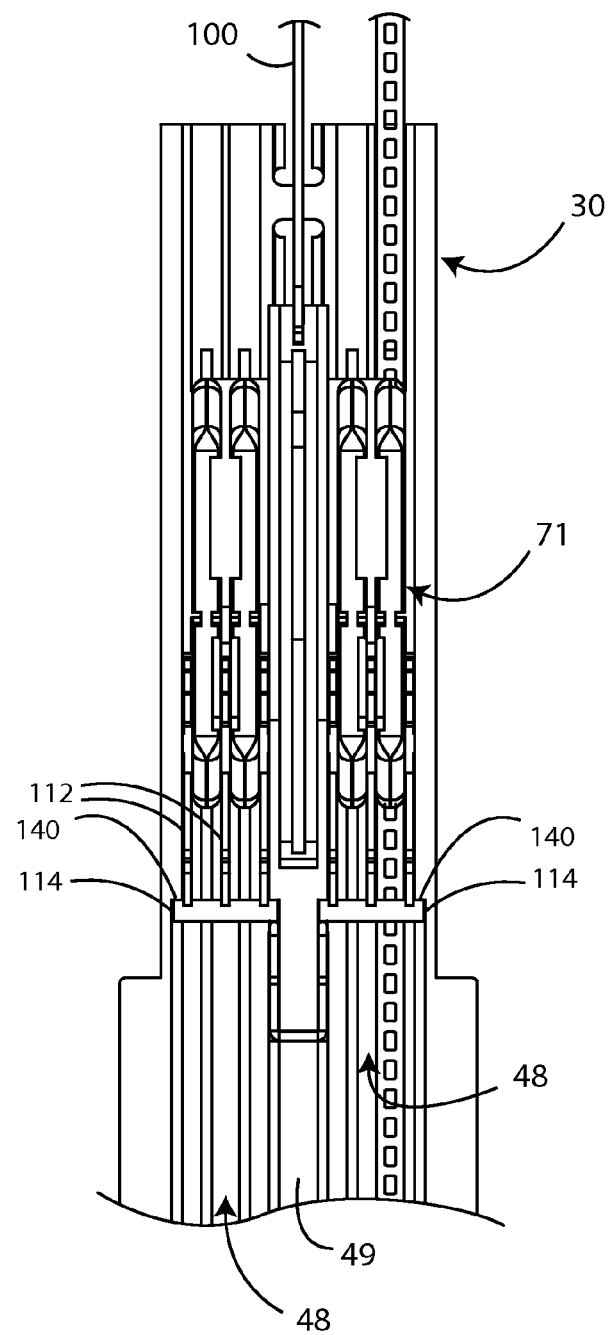
FIG. 20 is a top view of the active wedge of FIG. 15 in the first position of FIG. 18.

Referring to FIGS. 18 and 20, the active wedge 71 is in an initial position, in a first configuration. The initial position of the active wedge 71 in the staple holder 30 is proximal to the apertures 62 therein, and proximal to the staples 18 to be deployed. In the first position, the knife 124 may extend through the knife slot 64, such that part of the sharp edge 126 is located above the knife slot 64 and part of the sharp edge 126 is located below the knife slot 64; advantageously the sharp edge 126 is located proximal to tissue 148 and does not contact tissue 148 in the first position. The "first configuration" refers to a position of each wedge grate 110 relative to the wedge base 70. The first configuration also may be referred to as the "wedge down" configuration. In the first configuration, the entirety of the wedge grate 110 is positioned below the upper surface 74 of the wedge base 70. Also in the first configuration, the cross pin 114 of each wedge grate 110 is positioned proximal to the peak 132 of the proximal wedge catch 130. Further, the cross pin 114 of each wedge grate 110 may be positioned at the proximal end of a corresponding channel 48 defined in the bottom inner surface 49 of the staple holder 30. Advantageously, referring also to FIG. 10, at least one cross pin 114 rests on at least one step 50 defined in a channel 48. In this way, the cross pin 114 may be vertically spaced above the bottom inner surface 49 of the staple holder 30. Alternately, at least one cross pin 114 may slide along the bottom of a corresponding channel 48. Advantageously, when the active wedge 71 is in the first position and the first configuration, the cross pin 114 is held between the peak 132 of the proximal wedge catch 130 and a proximal wall 140 of the corresponding channel 48, where the proximal wall 140 extends inward from the outermost portion of the laterally-outermost step 50 and thereby prevents proximal motion of the cross pin 114 beyond that proximal wall 140. Referring also to FIGS. 13 and 17, in the first configuration, each pin 122 extending from a corresponding wedge plate 112 may be positioned at the distal end 84 of the corresponding channel 82 defined in a bulkhead 72 of the wedge base 70. Further, referring also to FIG. 22, an upper channel surface 142 is spaced vertically from the bottom inner surface 49 of the staple holder 30, and prevents the cross pin 114 from moving substantially upward. That is, aside from a small amount of play to allow the cross pin 114 to slide longitudinally, the cross pin 114 is vertically constrained between the upper channel surface 142 and the step 50.

The user then actuates one or more controls on the handle 8 to actuate the end effector 4. As a result, the actuation band 100 is moved distally, by any suitable mechanism or method. As one example, the proximal end of the actuation band 100 may extend near to or into the handle 8, and a mechanism within the handle 8 urges the actuation band 100 distally. The mechanism may be actuated by a release of energy stored within the handle 8. A mechanism for moving a actuation band 100 linearly is standard; any suitable mechanism or mechanisms may be utilized. Distal motion of the actuation band 100 in turn urges the active wedge 71 distally, due to the attachment between the actuation band 100 and the boss 90.

As the active wedge 71 is urged distally, each cross pin 114 of a wedge grate 110 is urged distally as well. However, each peak 132 of the proximal wedge catch 130 resists the distal motion of the corresponding cross pin 114, because each peak 132 is distal to and in the path of the cross pin 114, which in turn is constrained to move substantially longitudinally and not vertically. Consequently, each cross pin 114 does not immediately ride up over the corresponding peak 132, but rather is pushed longitudinally against the proximal wedge catch 130, which acts against the distal force applied to the active wedge 71. As a result, each cross pin 114 is held in place while the wedge base 70 advances distally. This relative motion between the cross pin 114 and the wedge base 70 urges each pin 122 extending from a corresponding wedge plate 112 out of the distal end of the corresponding channel 82 in the wedge base 70, referring also to FIG. 13. Each pin 122 then slides up the central segment 86 of the channel 82, until that pin 122 is caught by and stops in the detent 88 in the channel 82. As a result of this motion of the pins 122, the wedge plate 112 and thus the wedge grate 110 as a whole moves upward relative to the wedge base 70 to the second configuration.

Figure 21:
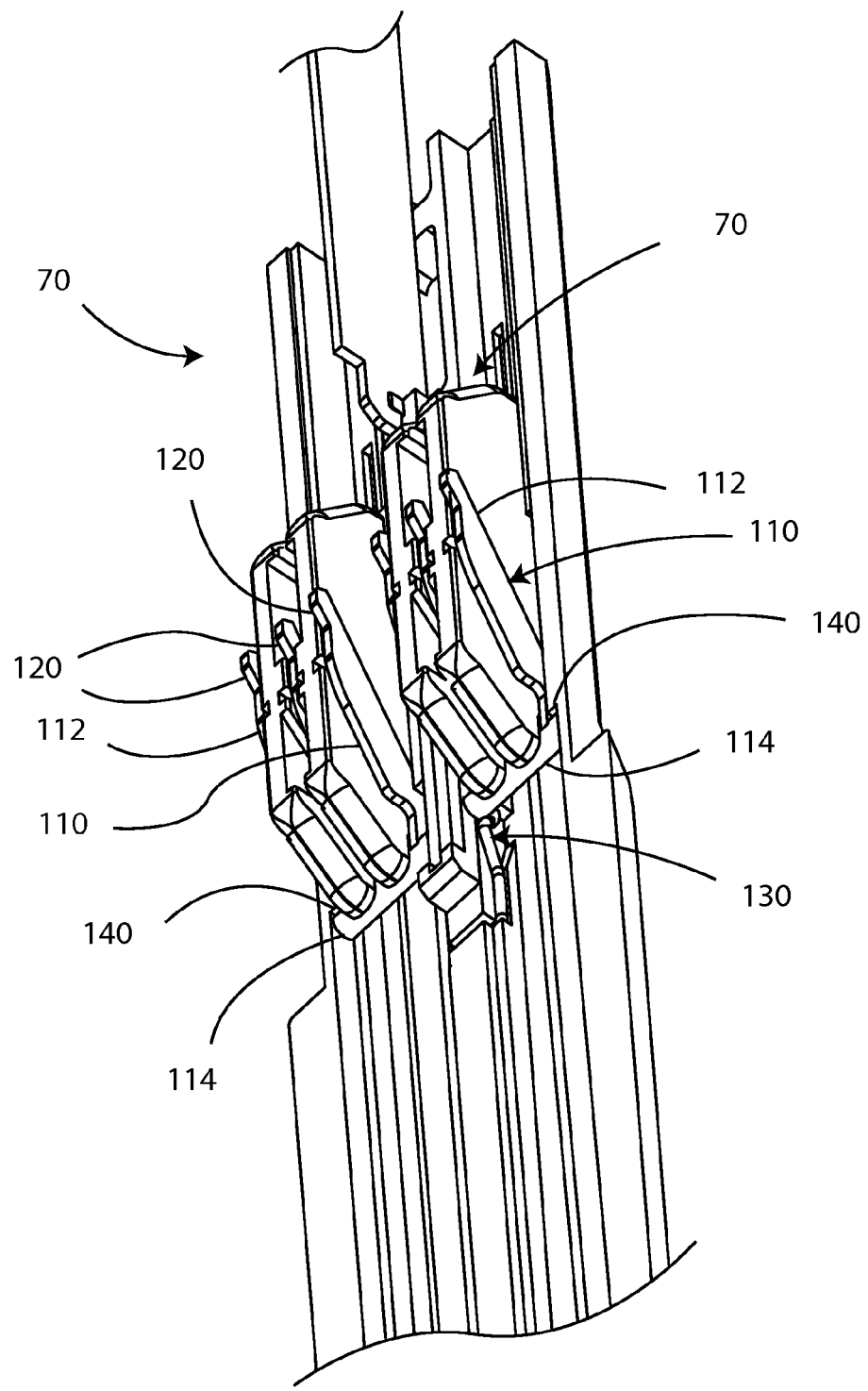
FIG. 21 is a perspective view of the active wedge of FIG. 15 at the first position within the staple holder, in a second configuration.

Referring to FIGS. 21-22, the "second configuration" means that at least part of at least one wedge plate 112 is positioned above the upper surface 74 of the wedge base 70. The second configuration may be referred to as the "wedge up" configuration as well. Advantageously, in the second configuration, at least part of the separation surface 120 of each wedge plate 112 is positioned above the upper surface 74 of the wedge base 70. The wedge base 70 is still substantially positioned at the initial position, and each cross pin 114 is still located between the corresponding peak 132 of the proximal wedge catch 130 and the proximal wall 140 of the corresponding channel 48. The actuation band 100 continues to apply a force in the distal direction to the active wedge 71. Because the wedge grate 110 can no longer move relative to the wedge base 70, that distal force applied to the active wedge 71 causes each crossbar 114 to push the proximal end of the proximal wedge catch 130 downward. This may be facilitated by a distally-sloped upward bend or angle in the proximal wedge catch 130 proximal to each peak. That is, the force applied to the proximal wedge catch 130 by the active wedge 71 grows large enough to push the proximal wedge catch 130 out of the path of motion of the wedge grate 110.

At that time, the active wedge 71 is free to move distally, sliding longitudinally along the channels 48 defined in the bottom inner surface 49 of the staple holder 30. Distal motion of the active wedge 71 causes deployment of the staples 18. For clarity, motion of a single wedge plate 112 to deploy one or more staples 18 in a corresponding row 26 is described.

Referring also to FIGS. 3-5 and 6-8, the active wedge 71 is initially proximal to the staples 18 in the corresponding generally-linear row 26, and the path of motion of each wedge plate 112 may be generally parallel to or collinear with the corresponding row 26. Referring also to FIGS. 16-17, as the wedge plate 112 moves distally, the encounter surface 116 of the wedge plate 112 contacts the most-proximal staple 18 in the corresponding row. Contact between the encounter surface 116 and the staple 18 applies force to the staple 18. Because the encounter surface 116 is substantially vertical, that force applied to the staple 18 is exerted in substantially a distal, longitudinal direction substantially normal to the encounter surface 116. This force is applied to the leg 20 or portion of the smooth curve of the staple 18 that is located closer to the tab 28 than to the free end 22. As a result, the distal force applied to the staple 18 results in a moment about the tab 28 or other frangible connection that connects the staple 18 to the feeder belt 16. The moment acts on the staple 18 to rotate the staple 18 about the tab 28, such that the free end 22 of the staple 18 moves upward, out of the corresponding aperture 62 in the upper surface 60 of the staple holder 30 and into the blood vessel 148 or other tissue clamped between the anvil 32 and the staple holder 30. During motion of the active wedge 71, the feeder belt 16 may be held substantially in place.

The active wedge 71 continues to slide distally, such that the encounter surface 116 of the wedge plate 112 exerts a force on the staple 18 that causes a moment about the tab 28. As the staple 18 rotates about the tab 28, and the wedge plate 112 continues to move distally, the lowest point of the staple 18 moves upward. When the lowest point of the staple 18 moves above the encounter surface 116, the deformation surface 118 begins to contact the staple 18. The deformation surface 118 is angled and/or curved upward in the proximal direction such that contact between that deformation surface 118 and the staple 18 continues to cause a moment about the tab 28 such that the staple 18 continues to rotate upward about the tab 28. As the free end 22 of the staple 18 rotates upward, it penetrates completely through the blood vessel 148 and then contacts the lower surface of the anvil 32. Optionally, a standard staple bending feature may be defined in the anvil 32 at the location where the free end 22 of the staple 18 contacts the anvil 32. As the free end 22 of the staple 18 contacts the anvil 32, the rotation of the staple 18 about the tab 28 results in motion of the free end 2 both upward and distally. However, contact between the free end 22 of the staple 18 and the anvil 32 prevents further upward motion of the free end 22 of the staple 18. As a result, the free end 22 of the staple 18 moves distally along the lower surface of the anvil 32 and/or staple bending feature defined thereon. This motion may bend or deform the leg 20 of the staple 18 associated with the free end 22, closing the staple 18 to form a D-shape or other suitable shape. The staple 18 may be fabricated from a plastically-deformable material such as stainless steel, such that deformation of the staple 18 may be plastic deformation. Alternately, at least part of at least one staple 18 may be elastically deformable or superelastically deformable.

As the active wedge 71 continues to move distally, the separation surface 120 of the wedge plate 112 slides distally toward the tab 28. As seen in FIG. 22, the top of the separation surface 120 extends above the upper surface 74 of the wedge base 70, and may extend above the upper surface of the feeder belt 16. As the separation surface 120 contacts the tab 28 during the longitudinal travel of the active wedge 71, it applies a force to the tab 28. As a result of the rotation of the staple 18 at its point of connection to the feeder belt 16, that connection may have experienced work hardening and become more brittle. As the separation surface 120 of the wedge plate 112 contacts and applies force to the tab 28, the that force applied by the separation surface 120 breaks or shears the staple 18 from the feeder belt 16 at the tab 28. Where the staple 18 and/or tab 28 include a weakened area at or near their intersection, the staple 18 may shear, break or otherwise separate from the feeder belt 16 at that weakened area. The separation surface 120 may be shaped to also actively push, urge or otherwise eject the staple 18 completely out of the staple holder 30. Alternately, the staple 18 is passively ejected from the staple holder 30, meaning that the staple 18 is not affirmatively urged out of the staple holder 30; rather, it is simply released from the staple holder 30 and allowed to exit therefrom. At this point, the deformed and ejected staple 18 is in position in the blood vessel 148. The frangibility of the staples 18 allows the staples 18 to be held securely and reliably by the feeder belt 16, and thus by the staple holder 30, while providing for reliable separation and deployment.

After the staple 18 has been separated from the feeder belt 16, the active wedge 71 continues its motion in the distal direction. As it does so, it encounters another staple 18, and deforms that staple 18 and separates that staple 18 from the feeder belt 16 in substantially the same manner as described above. The wedge grate 110 may be long enough that, as the wedge grate 110 has deformed one staple 18 a substantial amount but that staple 18 has not yet separated from the feeder belt 16, the wedge grate 110 engages and begins to deform the next most distal staple 18. Alternately, the wedge grate 110 is short enough that it completely deforms one staple 18, which is then ejected, before the wedge grate 110 engages and begins to deform the next most proximal staple 18. As the active wedge 71 moves distally, the knife 124 also slides distally along the knife slot 64, such that the sharp edge 126 of the knife 124 cuts the tissue held between the anvil 32 and staple holder 30. The knife 124 cuts tissue as the staples 18 are being deformed and ejected. Optionally, where the I-beam head 128 is fixed to the knife 124, that I-beam head 128 slides along a corresponding channel in the anvil 32, such that clamping is reinforced at or near the location of stapling as the active wedge 72 slides distally.

Figure 23:
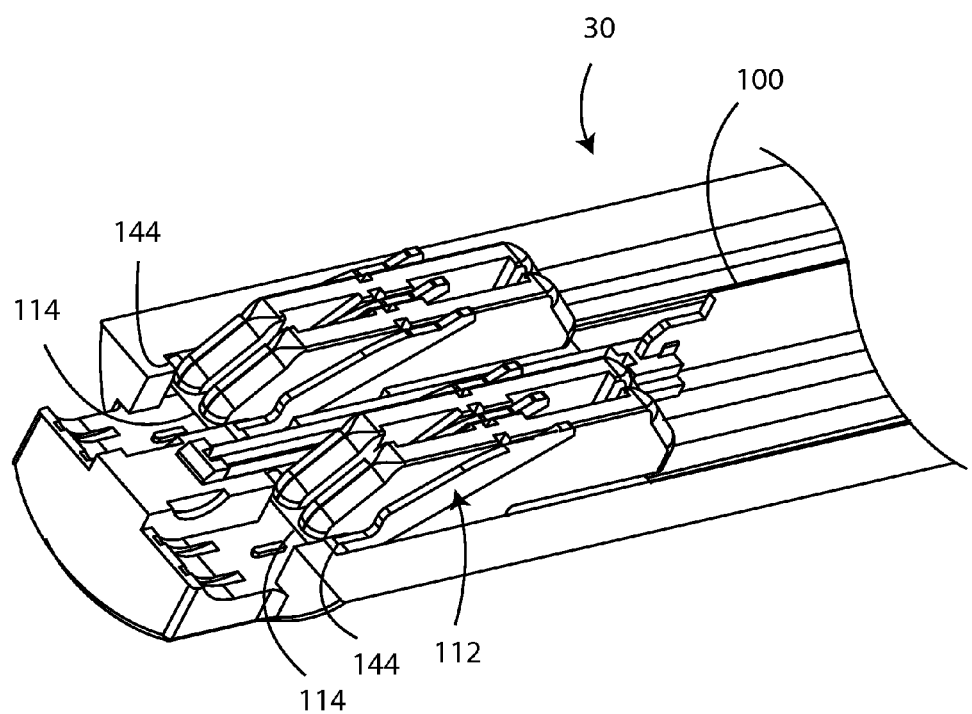
FIG. 23 is a perspective view of the active wedge of FIG. 15 in a second position within the staple holder, in the second configuration.

Referring to FIG. 23, the active wedge 71 may continue to move distally until the cross pin 114 of each wedge grate 110 encounters the distal wall 144 of the corresponding channel 48. Contact between each cross pin 114 and the corresponding distal wall 144 prevents further distal motion of the cross pin 114, and thus prevents further distal motion of the active wedge 71. Because the pins 122 of the wedge plates 112 are already in the corresponding detents 88 in the channels 82 in the wedge base 70, the wedge grate 110 cannot move further proximally relative to the wedge base 70 as a result of contact between the wedge grate 110 and the distal wall 144. This position of the active wedge 71 may be referred to as the second, final position, and the wedge grate 110 is still in the second configuration.

Figure 25:
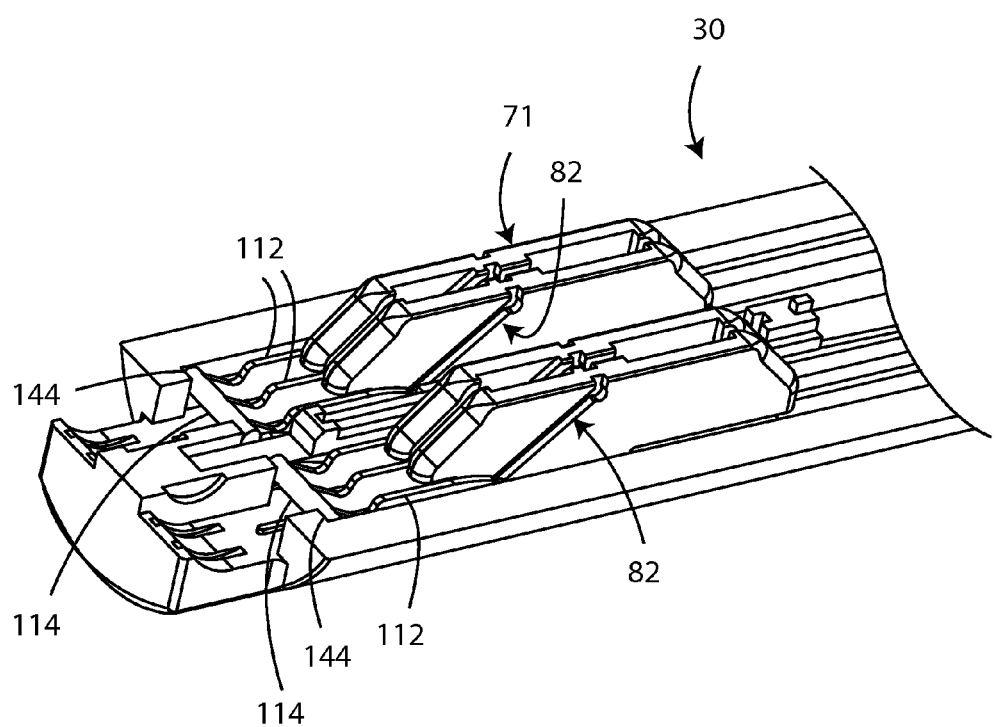
FIG. 25 is a perspective view of the active wedge of FIG. 15 in the second position within the staple holder, in the first configuration.

The endocutter 2 may then be reset for another firing. To do so, the actuation band 100 is retracted proximally such as by actuating one or more controls on the handle 8. As the band 100 moves proximally, it exerts a force in the proximal direction on the active wedge 71 and the wedge grate 110. When each cross pin 114 reaches the distal wall 144, the cross pin 114 may have already moved distally to the distal wedge catch 134, referring also to FIG. 24. The distal wedge catch 134 may include a portion proximal to its peak 136 that slopes gently upward in the distal direction, so that each cross pin 114 can push down the distal wedge catch 134 and slide over the peak 136 as it moves distally; after the cross pin 114 has moved distally to the peak 136, the peak 136 springs back upward. Thus, in the final position of the active wedge 71, each cross pin 114 may be held between the distal wall 144 and a peak 136 of the distal wedge catch 134. As the active wedge 71 is urged proximally, each cross pin 114 of a wedge grate 110 is urged proximally as well. However, each peak 136 of the distal wedge catch 134 resists the proximal motion of the corresponding cross pin 114, because each peak 136 is proximal to and in the path of the cross pin 114, which in turn is constrained to move substantially longitudinally and not vertically, as set forth above. Consequently, each cross pin 114 does not ride up over the corresponding peak 136 but rather is pulled longitudinally against the distal wedge catch 134, which acts against the distal force applied to the active wedge 71. As a result, each cross pin 114 is held in place while the wedge base 70 moves proximally. This relative motion between the cross pin 114 and the wedge base 70 urges each pin 122 extending from a corresponding wedge plate 112 distally out of the detent 88 in the corresponding channel in the wedge base 70, referring also to FIG. 13. Each pin then slides down the central segment 86 of the corresponding channel 82, until that pin 122 is caught by and stops in the distal end 84 of the corresponding channel 82. As a result of this motion of the pins 122, the wedge plates 112 and thus the wedge grate 110 as a whole moves downward relative to the wedge base 70 to the first configuration, as seen in FIG. 25. In the first, wedge-down configuration, each wedge grate 110 is below the upper surface 74 of the wedge base 70, such that the wedge grate 110 does not contact or otherwise engage the feeder belt 16 during motion of the wedge base 70 proximally.

Optionally, where the wedge base 70 includes one or more return arms 94, the return arms 94 may act to advance each feeder belt 16. The tooth 96 may be biased against the lower portion of the feeder belt 16. During advancement of the active wedge 71, the tooth 96 sequentially engages apertures 51 in the corresponding feeder belt 16, but due to the angled distal surface 99 of the tooth 96, the tooth 96 slides out of each aperture 51 as the angled distal surface 99 slides against the distal edge of each aperture 51, causing the cantilevered return arm 94 to flex upward. In this way, the return arms 94 do not cause motion of the feeder belts 16 during deployment of staples 18. However, as the wedge base 70 moves distally, the tooth 96 of each return arm 94 slides into an aperture 51 in the feeder belt 16 if those teeth 96 are not already located in apertures 51. As the wedge base 70 moves distally, the substantially vertical planar face 98 at the proximal end of each tooth 96 encounters the proximal end of the corresponding aperture 51. Because the face 98 is substantially vertical, and not angled to allow the tooth 96 to slip out, the face 98 engages the aperture 51, pushing the feeder belt 16 via the proximal edge of the corresponding aperture 51. Each feeder belt 16 is routed around a reversal wheel 42, along a path that starts generally straight and in the distal direction, then is curved downward along the surface of the corresponding reversal wheel 42, and then is generally straight and in the proximal direction, such that the reversal wheel 42 changes the direction of motion of the corresponding feeder belt 16 from generally distal to generally proximal. The portion of the feeder belt 16 located under and proximal to the reversal wheel 42 may be retracted proximally, thereby pulling the portion of the feeder belt 16 located above and proximal to the reversal wheel 42 in the distal direction and advancing fresh staples 18 into the housing 60. As the bottom portion of the feeder belt 16 is moved proximally by the return arm 94, the upper portion of the feeder belt 16 moves distally; this reversal of motion is caused by the wrapping of the feeder belts 16 about substantially half a circumference of the reversal wheels 42, as seen in FIGS. 10-11. Thus, as the wedge base 70 slides proximally back to its initial position, the return arms 94 cause the feeder belt 16 to advance a fresh set of unfired staples 18 into place within the staple holder 30. The motion of the feeder belt 16 that advances fresh staples 18 into position for firing may be referred to as "advancing" the feeder belt 16, regardless of the fact that part of the feeder belt 16 may be moved in a direction other than distally during that advancing.

As the active wedge 71 is urged proximally by proximal motion of the actuation band 100, each cross pin 114 of a wedge grate 110 is urged distally as well. However, each peak 136 of the distal wedge catch 134 resists the proximal motion of the corresponding cross pin 114, because each peak 136 is proximal to and in the path of the cross pin 114, which in turn is constrained to move substantially longitudinally and not vertically. Consequently, each cross pin 114 does not immediately ride up over the corresponding peak 134, but rather is pulled longitudinally against the distal wedge catch 134, which acts against the proximal force applied to the active wedge 71. As a result, each cross pin 114 is held in place while the wedge base 70 withdraws proximally. This relative motion between the cross pin 114 and the wedge base 70 urges each pin 122 extending from a corresponding wedge plate 112 out of the detent 88 at the proximal end of the corresponding channel 82 in the wedge base 70, referring also to FIG. 13. Each pin 122 then slides down the central segment 86 of the channel 82, until that pin 122 is caught by and stops at the distal end 84 of the channel 82. As a result of this motion of the pins 122, the wedge plate 112 and thus the wedge grate 110 as a whole moves downward relative to the wedge base 70 to the first, wedge-down configuration.

As set forth above, in the first, wedge-down configuration, each wedge plate 112 is positioned substantially below the upper surface 74 of the wedge base 70. The wedge base 70 is still substantially positioned at the final position, and each cross pin 114 is still located between the corresponding peak 136 of the distal wedge catch 134 and the distal wall 144 of the corresponding channel 48. The actuation band 100 continues to apply a force in the proximal direction to the active wedge 71. Because the wedge grate 110 can no longer move relative to the wedge base 70, that proximal force applied to the active wedge 71 causes each crossbar 114 to push the distal wedge catch 134 downward. This may be facilitated by a distally-sloped downward bend or angle in the distal wedge catch 134 distal to each peak. That is, the force applied to the distal wedge catch 134 by the active wedge 71 grows large enough to push the distal wedge catch 134 out of the path of motion of the wedge grate 110.

The active wedge 71 is then moved proximally until each cross pin 114 of the active wedge 71 reaches the proximal wall 140 of each channel 48 in the bottom inner surface 49 of the staple holder 30. Before it does so, each cross pin 114 may slide past the proximal wedge catch 130. The proximal wedge catch 130 may include a portion distal to its peak 136 that slopes gently upward in the proximal direction, so that each cross pin 114 can push down the proximal wedge catch 130 and slide over the peak 132 as it moves proximally; after the cross pin 114 has moved proximal to the peak 132, the peak 132 springs back upward.

Next, the end effector 4 may be actuated again at the option of the user, substantially as described above. In this way, the end effector 4 may be actuated multiple times without removing the end effector 4 through the trocar port 10 or other incision, structure or mechanism that allows access to the interior of the body of the patient. Keeping the end effector 4 within the body of the patient without withdrawing that end effector 4 through the trocar port 10 or other incision, structure or mechanism that allows access to the interior of the body of the patient may be referred to as maintaining the end effector within the body of the patient. The endocutter 2 may be actuated multiple times within the patient, without being removed from the patient, until the staples 18 in the endocutter 2 are exhausted. An indicator may be provided in the handle 8 or at another location in the endocutter 2 that shows how many unfired staples 18 remain in the endocutter 2.

Actuation of the endocutter 2 above has been generally described in terms of deployment and ejection of a single row 26 of staples 18 for clarity, where that deployment and ejection may be performed in substantially the same manner along each row 26 of staples 18. Operation of the endocutter 2 may be substantially as described above with regard to any number of rows 26 of staples 18 on a feeder belt 16, or any number of feeder belts 16.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus for use with a plurality of workpiece staples, comprising:
   a wedge base having an upper surface; and
   at least one wedge grate movable relative to said wedge base between a first position and a second position, wherein in said first position of said wedge base substantially all of said wedge grate is located below said upper surface of said wedge base, and wherein in said second position at least part of said wedge grate is positioned above said upper surface of said wedge base.

2. The surgical apparatus of claim 1, wherein said wedge grate includes a plurality of spaced-apart wedge plates, and a cross pin connected to each of said wedge plates.

3. The surgical apparatus of claim 2, wherein at least one wedge grate includes an encounter surface, a deformation surface proximal to said encounter surface, and a separation surface proximal to said deformation surface.

4. The surgical apparatus of claim 2, wherein said cross pin is located at a distal end of at least one wedge plate.

5. The surgical apparatus of claim 1, further comprising at least one channel defined in said wedge base; wherein at least one said wedge grate includes at least one pin positioned in and movable within said channel.

6. The surgical apparatus of claim 5, wherein said channel is angled upward in a proximal direction, and wherein said channel defines a detent at its most proximal location.

7. The surgical apparatus of claim 1, further comprising a knife fixed to said wedge base.

8. The surgical apparatus of claim 1, further comprising an actuation band fixed to said wedge base.

9. A surgical apparatus, comprising:
   an active wedge, comprising
      a wedge base, and
      at least one wedge grate movable relative to said wedge base between a first configuration and a second configuration; and
   a staple holder having at least one channel extending generally longitudinally therein, wherein said wedge base is slidable substantially longitudinally along a corresponding said channel.

10. The surgical apparatus of claim 9, wherein said wedge base is movable only substantially longitudinally along said corresponding channel in said staple holder, such that said corresponding channel substantially restricts vertical motion of said wedge base while allowing vertical motion of said wedge grate.

11. The surgical apparatus of claim 10, wherein said wedge grate is vertically movable between a first configuration in which substantially all of said wedge grate is located below said upper surface of said wedge base and a second configuration in which at least part of said wedge grate is positioned above said upper surface of said wedge base.

12. The surgical apparatus of claim 9, further comprising a proximal wedge catch located in proximity to a proximal end of at least one said channel in said staple holder, wherein said proximal wedge catch restrains said active wedge in a first position between said proximal wedge catch and a proximal wall of said channel.

13. The surgical apparatus of claim 12, wherein said wedge grate is movable distally from said initial position upon the application of a force large enough to push said proximal wedge catch out of the path of motion of said wedge grate.

14. The surgical apparatus of claim 9, further comprising a distal wedge catch located in proximity to a distal end of at least one said channel in said staple holder, wherein said distal wedge catch restrains said active wedge in a second position between said distal wedge catch and a distal wall of said channel.

15. The surgical apparatus of claim 14, wherein said wedge grate is movable proximally from said final position upon the application of a force large enough to push said distal wedge catch out of the path of motion of said wedge grate.

16. The surgical apparatus of claim 9, further comprising at least one feeder belt and a plurality of staples integral with said feeder belt, wherein said active wedge is movable relative to said feeder belt and said staples to deform said staples and break said staples from said feeder belt.

17. The surgical apparatus of claim 16, wherein substantially only the wedge grate portion of the active wedge participates in staple formation and separation.

18. The surgical apparatus of claim 16, wherein said wedge grate includes at least one wedge plate vertically movable between a first configuration in which substantially all of each said wedge plate is located below said upper surface of said wedge base and a second configuration in which at least part of at least one said wedge plate is positioned above said upper surface of said wedge base.

19. The surgical apparatus of claim 18, wherein, when said wedge grate is in said second configuration, said active wedge is movable longitudinally to sequentially deform a plurality of said staples and break said staples from said feeder belt.

20. The surgical apparatus of claim 19, wherein said wedge grate is movable back to said first configuration, after which said active wedge is movable longitudinally in the opposite direction to reset the apparatus.

* * * * *